(12) United States Patent
Luther et al.

(10) Patent No.: US 7,407,751 B2
(45) Date of Patent: Aug. 5, 2008

(54) METHODS FOR THE DETECTION AND PROGNOSIS OF BREAST TUMORS

(75) Inventors: Thomas Luther, Kleinröhrsdorf (DE); Viktor Magdolen, Kirchheim (DE); Manfred Schmitt, München (DE); Matthias Kotzsch, Dresden (DE)

(73) Assignee: Wilex AG, Munich (DE)

( * ) Notice: Subject to any disclaimer, the term of this patent is extended or adjusted under 35 U.S.C. 154(b) by 24 days.

(21) Appl. No.: 10/679,951

(22) Filed: Oct. 6, 2003

(65) Prior Publication Data

US 2004/0197863 A1  Oct. 7, 2004

Related U.S. Application Data

(63) Continuation-in-part of application No. PCT/EP02/03799, filed on Apr. 5, 2002.

(30) Foreign Application Priority Data

Apr. 6, 2001 (DE) ................. 101 17 381

(51) Int. Cl.
*C12Q 1/68* (2006.01)
*C07H 21/04* (2006.01)

(52) U.S. Cl. ........................... 435/6; 536/23.5

(58) Field of Classification Search ............. None
See application file for complete search history.

(56) References Cited

OTHER PUBLICATIONS

Kotzsch et al, 2005. European Journal of Cancer. 41: 2760-2768.*
Casey et al, 1994. Blood. 84(4): 1151-1156.*
Kalnina et al. 2005. Genes, Chromosomes and Cancer. 42: 342-357.*
Okumura et al. 2005. Biochemical and Biophysical Research Communictions. 334: 23-29.*
Allred et al, 2001. Endocrine-Related Cancer. 8: 47-61.*
Brinkman et al. 2004. Clinical Biochemistry. 37: 584-594.*
Luther et al, 2003. Thromb Haemost. 89(4): 705-717.*
Lacroix et al, 2004. Breast Cancer Research and Treatment. 83: 249-289.*
Kobaek-Larsen et al, 2000. Comp Med. 50(1): 16-26.*

* cited by examiner

*Primary Examiner*—Elizabeth C. Kemmerer
*Assistant Examiner*—Zachary C Howard
(74) *Attorney, Agent, or Firm*—Rothwell, Figg, Ernst & Manbeck PC

(57) ABSTRACT

This invention relates to the production of specific antibodies for the detection of human tumor associated urokinase-type plasminogen activator receptor (uPAR) deletion variants in biological samples as well as to their diagnostic and therapeutic application.

11 Claims, 26 Drawing Sheets

Ratio uPAR-del4/5 - vs. uPAR-2/3/4 mRNA

| Patients | <0.043[a] | 0.043 to 0.5 | >0.5[b] |
|---|---|---|---|
| total | 49 % | 26 % | 25 % |
| no disease recurrence (n=18)  47 % | 34 % | 8 % | 5 % |
| with disease recurrence (n=21)  53 % | 15 % | 18% | 20 % |

[a]*median*
[b]*in 4 cases the ratio was arbitrarily set to >1, although the detected uPAR-2/3/4 mRNA values (molecule number) was below the detection limit*

Figure 1

```
1/1                                              31/11
ATG GGT CAC CCG CCG CTG CTG CCG CTG CTG CTG CTG CTC CAC ACC TGC GTC CCA GCC TCT
 M   G   H   P   P   L   L   P   L   L   L   L   L   H   T   C   V   P   A   S
61/21                                            91/31
TGG GGC CTG CGG TGC ATG CAG TGT AAG ACC AAC GGG GAT TGC CGT GTG GAA GAG TGC GCC
 W   G   L   R   C   M   Q   C   K   T   N   G   D   C   R   V   E   E   C   A
121/41                                           151/51
CTG GGA CAG GAC CTC TGC AGG ACC ACG ATC GTG CGC TTG TGG GAA GAA GGA GAA GAG CTG
 L   G   Q   D   L   C   R   T   T   I   V   R   L   W   E   E   G   E   E   L
181/61                                           211/71
GAG CTG GTG GAG AAA AGC TGT ACC CAC TCA GAG AAG ACC AAC AGG ACC CTG AGC TAT CGG
 E   L   V   E   K   S   C   T   H   S   E   K   T   N   R   T   L   S   Y   R
241/81                                           271/91
ACT GGC TTG AAG ATC ACC AGC CTT ACC GAG GTT GTG TGT GGG TTA GAC TTG TGC AAC CAG
 T   G   L   K   I   T   S   L   T   E   V   V   C   G   L   D   L   C   N   Q
301/101                                          331/111
GGC AAC TCT GGG CGT CCA AAG GAT GAC CGC CAC CTC CGT GGC TGT GGC TAC CTT CCC GGC
 G   N   S   G   R   P   K   D   D   R   H   L   R   G   C   G   Y   L   P   G
361/121                                          391/131
TGC CCG GGC TCC AAT GGT TTC CAC AAC AAC GAC ACC TTC CAC TTC CTG AAA TGC TGC AAC
 C   P   G   S   N   G   F   H   N   N   D   T   F   H   F   L   K   C   C   N
421/141                                          451/151
ACC ACC AAA TGC AAC GAG GGC CCA ATC CTG GAG CTT GAA AAT CTG CCG CAG AAT GGC CGC
 T   T   K   C   N   E   G   P   I   L   E   L   E   N   L   P   Q   N   G   R
481/161                                          511/171
CAG TGT TAC AGC TGC AAG GGG AAC AGC ACC CAT GGA TGC TCC TCT GAA GAG ACT TTC CTC
 Q   C   Y   S   C   K   G   N   S   T   H   G   C   S   S   E   E   T   F   L
541/181                                          571/191
ATT GAC TGC CGA GGC CCC ATG AAT CAA TGT CTG GTA GCC ACC GGC ACT CAC GAA CCG AAA
 I   D   C   R   G   P   M   N   Q   C   L   V   A   T   G   T   H   E   P   K
601/201                                          631/211
AAC CAA AGC TAT ATG GTA AGA GGC TGT GCA ACC GCC TCA ATG TGC CAA CAT GCC CAC CTG
 N   Q   S   Y   M   V   R   G   C   A   T   A   S   M   C   Q   H   A   H   L
661/221                                          691/231
GGT GAC GCC TTC AGC ATG AAC CAC ATT GAT GTC TCC TGC TGT ACT AAA AGT GGC TGT AAC
 G   D   A   F   S   M   N   H   I   D   V   S   C   C   T   K   S   G   C   N
721/241                                          751/251
CAC CCA GAC CTG GAT GTC CAG TAC CGC AGT GGG GCT GCT CCT CAG CCT GGC CCT GCC CAT
 H   P   D   L   D   V   Q   Y   R   S   G   A   A   P   Q   P   G   P   A   H
781/261                                          811/271
CTC AGC CTC ACC ATC ACC CTG CTA ATG ACT GCC AGA CTG TGG GGA GGC ACT CTC CTC TGG
 L   S   L   T   I   T   L   L   M   T   A   R   L   W   G   G   T   L   L   W
841/281
ACC TAA
 T   *
```

Figure 2

```
1/1                                             31/11
ATG GGT CAC CCG CCG CTG CTG CCG CTG CTG CTG CTG CTC CAC ACC TGC GTC CCA GCC TCT
 M   G   H   P   P   L   L   P   L   L   L   L   L   H   T   C   V   P   A   S
61/21                                           91/31
TGG GGC CTG CGG TGC ATG CAG TGT AAG ACC AAC GGG GAT TGC CGT GTG GAA GAG TGC GCC
 W   G   L   R   C   M   Q   C   K   T   N   G   D   C   R   V   E   E   C   A
121/41                                          151/51
CTG GGA CAG GAC CTC TGC AGG ACC ACG ATC GTG CGC TTG TGG GAA GAA GGA GAA GAG CTG
 L   G   Q   D   L   C   R   T   T   I   V   R   L   W   E   E   G   E   E   L
181/61                                          211/71
GAG CTG GTG GAG AAA AGC TGT ACC CAC TCA GAG AAG ACC AAC AGG ACC CTG AGC TAT CGG
 E   L   V   E   K   S   C   T   H   S   E   K   T   N   R   T   L   S   Y   R
241/81                                          271/91
ACT GGC TTG AAG ATC ACC AGC CTT ACC GAG GTT GTG TGT GGG TTA GAC TTG TGC AAC CAG
 T   G   L   K   I   T   S   L   T   E   V   V   C   G   L   D   L   C   N   Q
301/101                                         331/111
GGC AAC TCT GTC CTG GAG CTT GAA AAT CTG CCG CAG AAT GGC CGC CAG TGT TAC AGC TGC
 G   N   S   V   L   E   L   E   N   L   P   Q   N   G   R   Q   C   Y   S   C
361/121                                         391/131
AAG GGG AAC AGC ACC CAT GGA TGC TCC TCT GAA GAG ACT TTC CTC ATT GAC TGC CGA GGC
 K   G   N   S   T   H   G   C   S   S   E   E   T   F   L   I   D   C   R   G
421/141                                         451/151
CCC ATG AAT CAA TGT CTG GTA GCC ACC GGC ACT CAC GAA CCG AAA AAC CAA AGC TAT ATG
 P   M   N   Q   C   L   V   A   T   G   T   H   E   P   K   N   Q   S   Y   M
481/161                                         511/171
GTA AGA GGC TGT GCA ACC GCC TCA ATG TGC CAA CAT GCC CAC CTG GGT GAC GCC TTC AGC
 V   R   G   C   A   T   A   S   M   C   Q   H   A   H   L   G   D   A   F   S
541/181                                         571/191
ATG AAC CAC ATT GAT GTC TCC TGC TGT ACT AAA AGT GGC TGT AAC CAC CCA GAC CTG GAT
 M   N   H   I   D   V   S   C   C   T   K   S   G   C   N   H   P   D   L   D
601/201                                         631/211
GTC CAG TAC CGC AGT GGG GCT GCT CCT CAG CCT GGC CCT GCC CAT CTC AGC CTC ACC ATC
 V   Q   Y   R   S   G   A   A   P   Q   P   G   P   A   H   L   S   L   T   I
661/221                                         691/231
ACC CTG CTA ATG ACT GCC AGA CTG TGG GGA GGC ACT CTC CTC TGG ACC TAA
 T   L   L   M   T   A   R   L   W   G   G   T   L   L   W   T   *
```

Figure 3

```
1/1                                         31/11
ATG GGT CAC CCG CCG CTG CTG CCG CTG CTG CTG CTG CTC CAC ACC TGC GTC CCA GCC TCT
 M   G   H   P   P   L   L   P   L   L   L   L   L   H   T   C   V   P   A   S
61/21                                       91/31
TGG GGC CTG CGG TGC ATG CAG TGT AAG ACC AAC GGG GAT TGC CGT GTG GAA GAG TGC GCC
 W   G   L   R   C   M   Q   C   K   T   N   G   D   C   R   V   E   E   C   A
121/41                                      151/51
CTG GGA CAG GAC CTC TGC AGG ACC ACG ATC GTG CGC TTG TGG GAA GAA GGA GAA GAG CTG
 L   G   Q   D   L   C   R   T   T   I   V   R   L   W   E   E   G   E   E   L
181/61                                      211/71
GAG CTG GTG GAG AAA AGC TGT ACC CAC TCA GAG AAG ACC AAC AGG ACC CTG AGC TAT CGG
 E   L   V   E   K   S   C   T   H   S   E   K   T   N   R   T   L   S   Y   R
241/81                                      271/91
ACT GGC TTG AAG ATC ACC AGC CTT ACC GAG GTT GTG TGT GGG Tta gac tTG TGC AAC CAG
 T   G   L   K   I   T   S   L   T   E   V   V   C   G   L   D   L   C   N   Q
301/101                                     331/111
GGC AAC TCT GGC CGG GCT GTC ACC TAT TCC CGA AGC CGT TAC CTC GAA TGC ATT TCC TGT
 G   N   S   G   R   A   V   T   Y   S   R   S   R   Y   L   E   C   I   S   C
361/121                                     391/131
GGC TCA TCA GAC ATG AGC TGT GAG AGG GGC CGG CAC CAG AGC CTG CAG TGC CGC AGC CCT
 G   S   S   D   M   S   C   E   R   G   R   H   Q   S   L   Q   C   R   S   P
421/141                                     451/151
GAA GAA CAG TGC CTG GAT GTG GTG ACC CAC TGG ATC CAG GAA GGT GAA GAA GTC CTG GAG
 E   E   Q   C   L   D   V   V   T   H   W   I   Q   E   G   E   E   V   L   E
481/161                                     511/171
CTT GAA AAT CTG CCG CAG AAT GGC CGC CAG TGT TAC AGC TGC AAG GGG AAC AGC ACC CAT
 L   E   N   L   P   Q   N   G   R   Q   C   Y   S   C   K   G   N   S   T   H
541/181                                     571/191
GGA TGC TCC TCT GAA GAG ACT TTC CTC ATT GAC TGC CGA GGC CCC ATG AAT CAA TGT CTG
 G   C   S   S   E   E   T   F   L   I   D   C   R   G   P   M   N   Q   C   L
601/201                                     631/211
GTA GCC ACC GGC ACT CAC GAA CCG AAA AAC CAA AGC TAT ATG GTA AGA GGC TGT GCA ACC
 V   A   T   G   T   H   E   P   K   N   Q   S   Y   M   V   R   G   C   A   T
661/221                                     691/231
GCC TCA ATG TGC CAA CAT GCC CAC CTG GGT GAC GCC TTC AGC ATG AAC CAC ATT GAT GTC
 A   S   M   C   Q   H   A   H   L   G   D   A   F   S   M   N   H   I   D   V
721/241                                     751/251
TCC TGC TGT ACT AAA AGT GGC TGT AAC CAC CCA GAC CTG GAT GTC CAG TAC CGC AGT GGG
 S   C   C   T   K   S   G   C   N   H   P   D   L   D   V   Q   Y   R   S   G
781/261                                     811/271
GCT GCT CCT CAG CCT GGC CCT GCC CAT CTC AGC CTC ACC ATC ACC CTG cta atg act gcc
 A   A   P   Q   P   G   P   A   H   L   S   L   T   I   T   L   L   M   T   A
841/281                                     871/291
aga ctg tgg gga ggc act ctc ctc tgg acc TAA
 R   L   W   G   G   T   L   L   W   T   *
```

Figure 4A

```
            .         20         .         40         .         60         .         80
  1 ATGGGTCACCCGCCGCTGCTGCCGCTGCTGCTGCTGCTCCACACCTGCGTCCCAGCCTCTTGGGGCCTGCGGTGCATGCA 80
    ||||||||||||||||||||||||||||||||||||||||||||||||||||||||||||||||||||||||||||||||
  1 ATGGGTCACCCGCCGCTGCTGCCGCTGCTGCTGCTGCTCCACACCTGCGTCCCAGCCTCTTGGGGCCTGCGGTGCATGCA 80
            .         20         .         40         .         60         .         80
            .        100         .        120         .        140         .        160
 81 GTGTAAGACCAACGGGGATTGCCGTGTGGAAGAGTGCGCCCTGGGACAGGACCTCTGCAGGACCACGATCGTGCGCTTGT 160
    ||||||||||||||||||||||||||||||||||||||||||||||||||||||||||||||||||||||||||||||||
 81 GTGTAAGACCAACGGGGATTGCCGTGTGGAAGAGTGCGCCCTGGGACAGGACCTCTGCAGGACCACGATCGTGCGCTTGT 160
            .        100         .        120         .        140         .        160
            .        180         .        200         .        220         .        240
161 GGGAAGAAGGAGAAGAGCTGGAGCTGGTGGAGAAAAGCTGTACCCACTCAGAGAAGACCAACAGGACCCTGAGCTATCGG 240
    ||||||||||||||||||||||||||||||||||||||||||||||||||||||||||||||||||||||||||||||||
161 GGGAAGAAGGAGAAGAGCTGGAGCTGGTGGAGAAAAGCTGTACCCACTCAGAGAAGACCAACAGGACCCTGAGCTATCGG 240
            .        180         .        200         .        220         .        240
            .        260         .        280         .        300
241 ACTGGCTTGAAGATCACCAGCCTTACCGAGGTTGTGTGTGGGTTAGACTTGTGCAACCAGGGCAACTCT---------- 309
    ||||||||||||||||||||||||||||||||||||||||||||||||||||||||||||||||||||||
241 ACTGGCTTGAAGATCACCAGCCTTACCGAGGTTGTGTGTGGGTTAGACTTGTGCAACCAGGGCAACTCTGGCCGGGCTGT 320
            .        260         .        280         .        300         .        320

321 CACCTATTCCCGAAGCCGTTACCTCGAATGCATTTCCTGTGGCTCATCAGACATGAGCTGTGAGAGGGGCCGGCACCAGA 400
            .        340         .        360         .        380         .        400
                                                                                .
310 ----------------------------------------------------------------------GGGCGTCCA 318
                                                                          |||||||||
401 GCCTGCAGTGCCGCAGCCCTGAAGAACAGTGCCTGGATGTGGTGACCCACTGGATCCAGGAAGGTGAAGAAGGGCGTCCA 480
            .        420         .        440         .        460         .        480
   320       .        340         .        360         .        380         .
319 AAGGATGACCGCCACCTCCGTGGCTGTGGCTACCTTCCCGGCTGCCCGGGCTCCAATGGTTTCCACAACAACGACACCTT 398
    ||||||||||||||||||||||||||||||||||||||||||||||||||||||||||||||||||||||||||||||||
481 AAGGATGACCGCCACCTCCGTGGCTGTGGCTACCTTCCCGGCTGCCCGGGCTCCAATGGTTTCCACAACAACGACACCTT 560
            .        500         .        520         .        540         .        560
   400       .        420         .        440         .        460         .
399 CCACTTCCTGAAATGCTGCAACACCACCAAATGCAACGAGGGCCCAATCCTGGAGCTTGAAAATCTGCCGCAGAATGGCC 478
    ||||||||||||||||||||||||||||||||||||||||||||||||||||||||||||||||||||||||||||||||
561 CCACTTCCTGAAATGCTGCAACACCACCAAATGCAACGAGGGCCCAATCCTGGAGCTTGAAAATCTGCCGCAGAATGGCC 640
            .        580         .        600         .        620         .        640
   480       .        500         .        520         .        540         .
479 GCCAGTGTTACAGCTGCAAGGGGAACAGCACCCATGGATGCTCCTCTGAAGAGACTTTCCTCATTGACTGCCGAGGCCCC 558
    ||||||||||||||||||||||||||||||||||||||||||||||||||||||||||||||||||||||||||||||||
641 GCCAGTGTTACAGCTGCAAGGGGAACAGCACCCATGGATGCTCCTCTGAAGAGACTTTCCTCATTGACTGCCGAGGCCCC 720
            .        660         .        680         .        700         .        720
   560       .        580         .        600         .        620         .
559 ATGAATCAATGTCTGGTAGCCACCGGCACTCACGAACCGAAAAACCAAAGCTATATGGTAAGAGGCTGTGCAACCGCCTC 638
    ||||||||||||||||||||||||||||||||||||||||||||||||||||||||||||||||||||||||||||||||
721 ATGAATCAATGTCTGGTAGCCACCGGCACTCACGAACCGAAAAACCAAAGCTATATGGTAAGAGGCTGTGCAACCGCCTC 800
            .        740         .        760         .        780         .        800
   640       .        660         .        680         .        700         .
639 AATGTGCCAACATGCCCACCTGGGTGACGCCTTCAGCATGAACCACATTGATGTCTCCTGCTGTACTAAAAGTGGCTGTA 718
    ||||||||||||||||||||||||||||||||||||||||||||||||||||||||||||||||||||||||||||||||
801 AATGTGCCAACATGCCCCACCTGGGTGACGCCTTCAGCATGAACCACATTGATGTCTCCTGCTGTACTAAAAGTGGCTGTA 880
            .        820         .        840         .        860         .        880
   720       .        740         .        760         .        780         .
719 ACCACCCAGACCTGGATGTCCAGTACCGCAGTGGGGCTGCTCCTCAGCCTGGCCCTGCCCATCTCAGCCTCACCATCACC 798
    ||||||||||||||||||||||||||||||||||||||||||||||||||||||||||||||||||||||||||||||||
881 ACCACCCAGACCTGGATGTCCAGTACCGCAGTGGGGCTGCTCCTCAGCCTGGCCCTGCCCATCTCAGCCTCACCATCACC 960
            .        900         .        920         .        940         .        960
   800       .        820         .        840
799 CTGCTAATGACTGCCAGACTGTGGGGAGGCACTCTCCTCTGGACCTAA                                  846
    ||||||||||||||||||||||||||||||||||||||||||||||||
961 CTGCTAATGACTGCCAGACTGTGGGGAGGCACTCTCCTCTGGACCTAA                                  1008
            .        980         .       1000

% Identity =  83.9 (846/1008)
```

Figure 4B

```
          •         20           •        40           •        60          •         80
  1  MGHPPLLPLLLLLHTCVPASWGLRCMQCKTNGDCRVEECALGQDLCRTTIVRLWEEGEELELVEKSCTHSEKTNRTLSYR 80
     MGHPPLLPLLLLLHTCVPASWGLRCMQCKTNGDCRVEECALGQDLCRTTIVRLWEEGEELELVEKSCTHSEKTNRTLSYR
  1  MGHPPLLPLLLLLHTCVPASWGLRCMQCKTNGDCRVEECALGQDLCRTTIVRLWEEGEELELVEKSCTHSEKTNRTLSYR 80
          •         20           •        40           •        60          •         80
                                  •        100
 81  TGLKITSLTEVVCGLDLCNQGNS--------------------------------------------------GRP   106
     TGLKITSLTEVVCGLDLCNQGNS                                                  GRP
 81  TGLKITSLTEVVCGLDLCNQGNSGRAVTYSRSRYLECISCGSSDMSCERGRHQSLQCRSPEEQCLDVVTHWIQEGEEGRP 160
                                  •        100          •        120         •        140          •       160
          •        120           •       140           •       160          •         180
107  KDDRHLRGCGYLPGCPGSNGFHNNDTFHFLKCCNTTKCNEGPILELENLPQNGRQCYSCKGNSTHGCSSEETFLIDCRGP 186
     KDDRHLRGCGYLPGCPGSNGFHNNDTFHFLKCCNTTKCNEGPILELENLPQNGRQCYSCKGNSTHGCSSEETFLIDCRGP
161  KDDRHLRGCGYLPGCPGSNGFHNNDTFHFLKCCNTTKCNEGPILELENLPQNGRQCYSCKGNSTHGCSSEETFLIDCRGP 240
                                  •        180          •        200         •        220          •       240
          •        200           •       220           •       240          •         260
187  MNQCLVATGTHEPKNQSYMVRGCATASMCQHAHLGDAFSMNHIDVSCCTKSGCNHPDLDVQYRSGAAPQPGPAHLSLTIT 266
     MNQCLVATGTHEPKNQSYMVRGCATASMCQHAHLGDAFSMNHIDVSCCTKSGCNHPDLDVQYRSGAAPQPGPAHLSLTIT
241  MNQCLVATGTHEPKNQSYMVRGCATASMCQHAHLGDAFSMNHIDVSCCTKSGCNHPDLDVQYRSGAAPQPGPAHLSLTIT 320
                                  •        260          •        280         •        300          •       320
          •        280
267  LLMTARLWGGTLLWT*                                                                 282
     LLMTARLWGGTLLWT*
321  LLMTARLWGGTLLWT*                                                                 336

% Identity = 83.9 (282/336)
```

Figure 5A

```
              •         20         •         40         •         60         •         80
    1 ATGGGTCACCCGCCGCTGCTGCCGCTGCTGCTGCTGCTCCACACCTGCGTCCCAGCCTCTTGGGGCCTGCGGTGCATGCA  80
      ||||||||||||||||||||||||||||||||||||||||||||||||||||||||||||||||||||||||||||||||
    1 ATGGGTCACCCGCCGCTGCTGCCGCTGCTGCTGCTGCTCCACACCTGCGTCCCAGCCTCTTGGGGCCTGCGGTGCATGCA  80
              •         20         •         40         •         60         •         80
              •        100         •        120         •        140         •        160
   81 GTGTAAGACCAACGGGGATTGCCGTGTGGAAGAGTGCGCCCTGGGACAGGACCTCTGCAGGACCACGATCGTGCGCTTGT 160
      ||||||||||||||||||||||||||||||||||||||||||||||||||||||||||||||||||||||||||||||||
   81 GTGTAAGACCAACGGGGATTGCCGTGTGGAAGAGTGCGCCCTGGGACAGGACCTCTGCAGGACCACGATCGTGCGCTTGT 160
              •        100         •        120         •        140         •        160
              •        180         •        200         •        220         •        240
  161 GGGAAGAAGGAGAAGAGCTGGAGCTGGTGGAGAAAAGCTGTACCCACTCAGAGAAGACCAACAGGACCCTGAGCTATCGG 240
      ||||||||||||||||||||||||||||||||||||||||||||||||||||||||||||||||||||||||||||||||
  161 GGGAAGAAGGAGAAGAGCTGGAGCTGGTGGAGAAAAGCTGTACCCACTCAGAGAAGACCAACAGGACCCTGAGCTATCGG 240
              •        180         •        200         •        220         •        240
              •        260         •        280         •        300         •
  241 ACTGGCTTGAAGATCACCAGCCTTACCGAGGTTGTGTGTGGGTTAGACTTGTGCAACCAGGGCAACTCTG----------  310
      |||||||||||||||||||||||||||||||||||||||||||||||||||||||||||||||||||||
  241 ACTGGCTTGAAGATCACCAGCCTTACCGAGGTTGTGTGTGGGTTAGACTTGTGCAACCAGGGCAACTCTGGCCGGGCTGT 320
              •        260         •        280         •        300         •        320

321 CACCTATTCCCGAAGCCGTTACCTCGAATGCATTTCCTGTGGCTCATCAGACATGAGCTGTGAGAGGGGCCGGCACCAGA 400
              •        340         •        360         •        380         •        400

401 GCCTGCAGTGCCGCAGCCCTGAAGAACAGTGCCTGGATGTGGTGACCCACTGGATCCAGGAAGGTGAAGAAGGGCGTCCA 480
              •        420         •        440         •        460         •        480

481 AAGGATGACCGCCACCTCCGTGGCTGTGGCTACCTTCCCGGCTGCCCGGGCTCCAATGGTTTCCACAACAACGACACCTT 560
              •        500         •        520         •        540         •        560
                                                                 •        320         •        340
  311 -----------------------------------TCCTGGAGCTTGAAAATCTGCCGCAGAATGGCC 343
                                         |||||||||||||||||||||||||||||||||||
  561 CCACTTCCTGAAATGCTGCAACACCACCAAATGCAACGAGGGCCCAATCCTGGAGCTTGAAAATCTGCCGCAGAATGGCC 640
              •        580         •        600         •        620         •        640
              •        360         •        380         •        400         •        420
  344 GCCAGTGTTACAGCTGCAAGGGGAACAGCACCCATGGATGCTCCTCTGAAGAGACTTTCCTCATTGACTGCCGAGGCCCC 423
      ||||||||||||||||||||||||||||||||||||||||||||||||||||||||||||||||||||||||||||||||
  641 GCCAGTGTTACAGCTGCAAGGGGAACAGCACCCATGGATGCTCCTCTGAAGAGACTTTCCTCATTGACTGCCGAGGCCCC 720
              •        660         •        680         •        700         •        720
              •        440         •        460         •        480         •        500
  424 ATGAATCAATGTCTGGTAGCCACCGGCACTCACGAACCGAAAAACCAAAGCTATATGGTAAGAGGCTGTGCAACCGCCTC 503
      ||||||||||||||||||||||||||||||||||||||||||||||||||||||||||||||||||||||||||||||||
  721 ATGAATCAATGTCTGGTAGCCACCGGCACTCACGAACCGAAAAACCAAAGCTATATGGTAAGAGGCTGTGCAACCGCCTC 800
              •        740         •        760         •        780         •        800
              •        520         •        540         •        560         •        580
  504 AATGTGCCAACATGCCCACCTGGGTGACGCCTTCAGCATGAACCACATTGATGTCTCCTGCTGTACTAAAAGTGGCTGTA 583
      ||||||||||||||||||||||||||||||||||||||||||||||||||||||||||||||||||||||||||||||||
  801 AATGTGCCAACATGCCCACCTGGGTGACGCCTTCAGCATGAACCACATTGATGTCTCCTGCTGTACTAAAAGTGGCTGTA 880
              •        820         •        840         •        860         •        880
              •        600         •        620         •        640         •        660
  584 ACCACCCAGACCTGGATGTCCAGTACCGCAGTGGGGCTGCTCCTCAGCCTGGCCCTGCCCATCTCAGCCTCACCATCACC 663
      ||||||||||||||||||||||||||||||||||||||||||||||||||||||||||||||||||||||||||||||||
  881 ACCACCCAGACCTGGATGTCCAGTACCGCAGTGGGGCTGCTCCTCAGCCTGGCCCTGCCCATCTCAGCCTCACCATCACC 960
              •        900         •        920         •        940         •        960
              •        680         •        700         •
  664 CTGCTAATGACTGCCAGACTGTGGGGAGGCACTCTCCTCTGGACCTAA                                  711
      |||||||||||||||||||||||||||||||||||||||||||||||
  961 CTGCTAATGACTGCCAGACTGTGGGGAGGCACTCTCCTCTGGACCTAA                                 1008
              •        980         •       1000

% Identity = 70.5 (711/1008)
```

Figure 5B

```
                 •         20         •         40         •         60         •         80
     1 MGHPPLLPLLLLLHTCVPASWGLRCMQCKTNGDCRVEECALGQDLCRTTIVRLWEEGEELELVEKSCTHSEKTNRTLSYR 80
       MGHPPLLPLLLLLHTCVPASWGLRCMQCKTNGDCRVEECALGQDLCRTTIVRLWEEGEELELVEKSCTHSEKTNRTLSYR
     1 MGHPPLLPLLLLLHTCVPASWGLRCMQCKTNGDCRVEECALGQDLCRTTIVRLWEEGEELELVEKSCTHSEKTNRTLSYR 80
                 •         20         •         40         •         60         •         80
                                                •        100
    81 TGLKITSLTEVVCGLDLCNQGNS--------------------------------------------------------- 103
       TGLKITSLTEVVCGLDLCNQGNS
    81 TGLKITSLTEVVCGLDLCNQGNSGRAVTYSRSRYLECISCGSSDMSCERGRHQSLQCRSPEEQCLDVVTHWIQEGEEGRP 160
                 •        100         •        120         •        140         •        160
                                                                   •        120         •        140
   104 ---------------------------------------VLELENLPQNGRQCYSCKGNSTHGCSSEETFLIDCRGP 141
                                              +LELENLPQNGRQCYSCKGNSTHGCSSEETFLIDCRGP
   161 KDDRHLRGCGYLPGCPGSNGFHNNDTFHFLKCCNTTKCNEGPILELENLPQNGRQCYSCKGNSTHGCSSEETFLIDCRGP 240
                 •        180         •        200         •        220         •        240
                 •        160         •        180         •        200         •        220
   142 MNQCLVATGTHEPKNQSYMVRGCATASMCQHAHLGDAFSMNHIDVSCCTKSGCNHPDLDVQYRSGAAPQPGPAHLSLTIT 221
       MNQCLVATGTHEPKNQSYMVRGCATASMCQHAHLGDAFSMNHIDVSCCTKSGCNHPDLDVQYRSGAAPQPGPAHLSLTIT
   241 MNQCLVATGTHEPKNQSYMVRGCATASMCQHAHLGDAFSMNHIDVSCCTKSGCNHPDLDVQYRSGAAPQPGPAHLSLTIT 320
                 •        260         •        280         •        300         •        320
                 •
   222 LLMTARLWGGTLLWT*                                                                 237
       LLMTARLWGGTLLWT*
   321 LLMTARLWGGTLLWT*                                                                 336
                 •

% Identity = 70.2 (236/336)
```

Figure 6A

```
              20              40              60              80
  1 ATGGGTCACCCGCCGCTGCTGCCGCTGCTGCTGCTGCTCCACACCTGCGTCCCAGCCTCTTGGGGCCTGCGGTGCATGCA  80
    ||||||||||||||||||||||||||||||||||||||||||||||||||||||||||||||||||||||||||||||||
  1 ATGGGTCACCCGCCGCTGCTGCCGCTGCTGCTGCTGCTCCACACCTGCGTCCCAGCCTCTTGGGGCCTGCGGTGCATGCA  80
              20              40              60              80
             100             120             140             160
 81 GTGTAAGACCAACGGGGATTGCCGTGTGGAAGAGTGCGCCCTGGGACAGGACCTCTGCAGGACCACGATCGTGCGCTTGT 160
    ||||||||||||||||||||||||||||||||||||||||||||||||||||||||||||||||||||||||||||||||
 81 GTGTAAGACCAACGGGGATTGCCGTGTGGAAGAGTGCGCCCTGGGACAGGACCTCTGCAGGACCACGATCGTGCGCTTGT 160
             100             120             140             160
             180             200             220             240
161 GGGAAGAAGGAGAAGAGCTGGAGCTGGTGGAGAAAAGCTGTACCCACTCAGAGAAGACCAACAGGACCCTGAGCTATCGG 240
    ||||||||||||||||||||||||||||||||||||||||||||||||||||||||||||||||||||||||||||||||
161 GGGAAGAAGGAGAAGAGCTGGAGCTGGTGGAGAAAAGCTGTACCCACTCAGAGAAGACCAACAGGACCCTGAGCTATCGG 240
             180             200             220             240
             260             280             300             320
241 ACTGGCTTGAAGATCACCAGCCTTACCGAGGTTGTGTGTGGGTtagactTGTGCAACCAGGGCAACTCTGGCCGGGCTGT 320
    ||||||||||||||||||||||||||||||||||||||||||| |||||||||||||||||||||||| |||||||||||
241 ACTGGCTTGAAGATCACCAGCCTTACCGAGGTTGTGTGTGGGTTAGACTTGTGCAACCAGGGCAACTCTGGCCGGGCTGT 320
             260             280             300             320
             340             360             380             400
321 CACCTATTCCCGAAGCCGTTACCTCGAATGCATTTCCTGTGGCTCATCAGACATGAGCTGTGAGAGGGGCCGGCACCAGA 400
    ||||||||||||||||||||||||||||||||||||||||||||||||||||||||||||||||||||||||||||||||
321 CACCTATTCCCGAAGCCGTTACCTCGAATGCATTTCCTGTGGCTCATCAGACATGAGCTGTGAGAGGGGCCGGCACCAGA 400
             340             360             380             400
             420             440             460
401 GCCTGCAGTGCCGCAGCCCTGAAGAACAGTGCCTGGATGTGGTGACCCACTGGATCCAGGAAGGTGAAGAAG-------- 472
    ||||||||||||||||||||||||||||||||||||||||||||||||||||||||||||||||||||||||
401 GCCTGCAGTGCCGCAGCCCTGAAGAACAGTGCCTGGATGTGGTGACCCACTGGATCCAGGAAGGTGAAGAAGGGCGTCCA 480
             420             440             460             480

-------------------------------------------------------------------------------

481 AAGGATGACCGCCACCTCCGTGGCTGTGGCTACCTTCCCGGCTGCCCGGGCTCCAATGGTTTCCACAACAACGACACCTT 560
             500             520             540             560
                                                        480             500
473 ---------------------------------------------TCCTGGAGCTTGAAAATCTGCCGCAGAATGGCC 505
                                                 |||||||||||||||||||||||||||||||||
561 CCACTTCCTGAAATGCTGCAACACCACCAAATGCAACGAGGGCCCAATCCTGGAGCTTGAAAATCTGCCGCAGAATGGCC 640
             580             600             620             640
         520             540             560             580
506 GCCAGTGTTACAGCTGCAAGGGGAACAGCACCCATGGATGCTCCTCTGAAGAGACTTTCCTCATTGACTGCCGAGGCCCC 585
    ||||||||||||||||||||||||||||||||||||||||||||||||||||||||||||||||||||||||||||||||
641 GCCAGTGTTACAGCTGCAAGGGGAACAGCACCCATGGATGCTCCTCTGAAGAGACTTTCCTCATTGACTGCCGAGGCCCC 720
             660             680             700             720
586 ATGAATCAATGTCTGGTAGCCACCGGCACTCACGAACCGAAAAACCAAAGCTATATGGTAAGAGGCTGTGCAACCGCCTC 665
    ||||||||||||||||||||||||||||||||||||||||||||||||||||||||||||||||||||||||||||||||
721 ATGAATCAATGTCTGGTAGCCACCGGCACTCACGAACCGAAAAACCAAAGCTATATGGTAAGAGGCTGTGCAACCGCCTC 800
             740             760             780             800
         680             700             720             740
666 AATGTGCCAACATGCCCACCTGGGTGACGCCTTCAGCATGAACCACATTGATGTCTCCTGCTGTACTAAAAGTGGCTGTA 745
    ||||||||||||||||||||||||||||||||||||||||||||||||||||||||||||||||||||||||||||||||
801 AATGTGCCAACATGCCCACCTGGGTGACGCCTTCAGCATGAACCACATTGATGTCTCCTGCTGTACTAAAAGTGGCTGTA 880
             820             840             860             880
         760             780             800             820
746 ACCACCCAGACCTGGATGTCCAGTACCGCAGTGGGGCTGCTCCTCAGCCTGGCCCTGCCCATCTCAGCCTCACCATCACC 825
    ||||||||||||||||||||||||||||||||||||||||||||||||||||||||||||||||||||||||||||||||
881 ACCACCCAGACCTGGATGTCCAGTACCGCAGTGGGGCTGCTCCTCAGCCTGGCCCTGCCCATCTCAGCCTCACCATCACC 960
             900             920             940             960
         840             860
826 CTGctaatgactgccagactgtggggaggcactctcctctggaccTAA                                873
    |||||||||||||||||||||||||||||||||||||||||||||||
961 CTGCTAATGACTGCCAGACTGTGGGGAGGCACTCTCCTCTGGACCTAA                               1008
             980            1000

% Identity = 86.6 (873/1008)
```

Figure 6B

```
              .         20          .         40          .         60          .         80
  1 MGHPPLLPLLLLLHTCVPASWGLRCMQCKTNGDCRVEECALGQDLCRTTIVRLWEEGEELELVEKSCTHSEKTNRTLSYR  80
    MGHPPLLPLLLLLHTCVPASWGLRCMQCKTNGDCRVEECALGQDLCRTTIVRLWEEGEELELVEKSCTHSEKTNRTLSYR
  1 MGHPPLLPLLLLLHTCVPASWGLRCMQCKTNGDCRVEECALGQDLCRTTIVRLWEEGEELELVEKSCTHSEKTNRTLSYR  80
              .         20          .         40          .         60          .         80
              .        100          .        120          .        140          .
 81 TGLKITSLTEVVCGLDLCNQGNSGRAVTYSRSRYLECISCGSSDMSCERGRHQSLQCRSPEEQCLDVVTHWIQEGEE--- 157
    TGLKITSLTEVVCGLDLCNQGNSGRAVTYSRSRYLECISCGSSDMSCERGRHQSLQCRSPEEQCLDVVTHWIQEGEE
 81 TGLKITSLTEVVCGLDLCNQGNSGRAVTYSRSRYLECISCGSSDMSCERGRHQSLQCRSPEEQCLDVVTHWIQEGEEGRP 160
              .        100          .        120          .        140          .        160
                                                      .        160          .        180          .
158 ---------------------------------------VLELENLPQNGRQCYSCKGNSTHGCSSEETFLIDCRGP 195
                                           +LELENLPQNGRQCYSCKGNSTHGCSSEETFLIDCRGP
161 KDDRHLRGCGYLPGCPGSNGFHNNDTFHFLKCCNTTKCNEGPILELENLPQNGRQCYSCKGNSTHGCSSEETFLIDCRGP 240
              .        180          .        200          .        220          .        240
              .        200          .        220          .        240          .        260
196 MNQCLVATGTHEPKNQSYMVRGCATASMCQHAHLGDAFSMNHIDVSCCTKSGCNHPDLDVQYRSGAAPQPGPAHLSLTIT 275
    MNQCLVATGTHEPKNQSYMVRGCATASMCQHAHLGDAFSMNHIDVSCCTKSGCNHPDLDVQYRSGAAPQPGPAHLSLTIT
241 MNQCLVATGTHEPKNQSYMVRGCATASMCQHAHLGDAFSMNHIDVSCCTKSGCNHPDLDVQYRSGAAPQPGPAHLSLTIT 320
              .        260          .        280          .        300          .        320
              .        280          .
276 LLMTARLWGGTLLWT*                                                                 291
    LLMTARLWGGTLLWT*
321 LLMTARLWGGTLLWT*                                                                 336
              .

% Identity = 86.3 (290/336)
```

Figure 10

| uPARdel4+5 | Q | G | N | S | V | L | E | L |
|---|---|---|---|---|---|---|---|---|
| uPARdel4 | Q | G | N | S | G | R | P | K |
| uPARdel5 | E | G | E | E | V | L | E | L |

Figure 12

| | Ec-uPAR1-283 | uPAR-del4 | uPAR-del45 | uPAR-del5 |
|---|---|---|---|---|
| Kan1-del4 | ++ | +++ | - | ++ |
| Kan2-del45 | ++ | ++ | +++ | +++ |
| Huhn1-del4 | - | ++ | + | + |
| Huhn1-del5 | - | - | - | +++ |
| Huhn2-del45 | ++ | ++ | ++ | ++ |
| Mee1-del5 | + | + | + | +++ |

Figure 13

Sandwich-ELISA with cell lysates and tumor extracts*

| Probe | Dilution | Kan. (1)-anti del4/5 IgG | Kan. (1)-anti del4# IgG | Kan. (2)-anti del4/5 IgG | Kan. (2)-anti del4 IgG | Huhn. (1)-anti del4/5 IgG | Huhn. (1)-anti del4 IgG | HU/IIIF10** | HU/HD13** |
|---|---|---|---|---|---|---|---|---|---|
| MaCa-ZLL | | | | | | | | | |
| aMCF-7 | 01:20 | 0,3 | v | 0,25 | v | 0,4 | v | 1,0 | 0,4 |
| T47D | 01:20 | 0,2 | v | 0,35 | 0,25 | 0,5 | 0,2 | 0,35 | v |
| MCF-7 | 01:20 | 0,5 | v | 0,6 | 0,4 | 0,95 | 0,3 | 1,2 | 0,2 |
| HaCaT | 01:20 | v | v | v | v | v | v | v | v |
| BT549 | 01:20 | 0,4 | v | nt | nt | nt | nt | 0,4 | 0,15 |
| MaCa-extracts | | | | | | | | | |
| 986 | 01:10 | 0,4 | v | 0,3 | v | 0,4 | 0,15 | 1,6 | 1,3 |
| 993 | 01:10 | 1,3 | v | 1,0 | 0,3 | 1,3 | 0,45 | 1,25 | 0,75 |
| 997 | 01:10 | 0,4 | v | 0,3 | v | 0,4 | v | 0,5 | 0,25 |
| 998 | 01:10 | 0,2 | v | 0,15 | v | v | v | 0,8 | 0,3 |
| 999 | 01:10 | v | v | v | v | v | v | v | 0,5 |
| 1000 | 01:10 | 0,25 | v | 0,15 | 0,15 | 0,6 | 0,2 | 0,4 | 0,2 |
| 1001 | 01:10 | 0,6 | v | 0,45 | 0,2 | 0,6 | 0,25 | 0,8 | 0,5 |
| 1016 | 01:10 | 0,6 | v | 0,6 | v | 0,6 | v | 0,7 | 0,5 |
| OvCa II | 01:40 | v | v | v | v | v | v | 1,2 | 0,5 |
| OvCa III | 01:40 | 0,5 | v | 0,6 | 0,2 | 0,6 | 0,25 | 8,4 | 4,2 |
| OvCa IV | 01:40 | 0,2 | v | v | v | v | v | 0,6 | v |
| OvCa V | 01:40 | 0,5 | v | 0,5 | 0,2 | 0,65 | 0,25 | 4,5 | 0,8 |
| EE Stand. | high | 1000 | 1700 | 1100 | 1600 | 900 | 1400 | | |
| EE Stand. | low | 150 | 400 | 150 | 150 | 130 | 120 | | |
| EE Background | | 110 | 190 | 130 | 100 | 90 | 90 | | |

* relativ uPAR-conc. Compared to resp. E.coli uPAR-variants
** ng/ml
Kan.(1)-anti-del4 does not react with E.coli del4/5 in WB + EIA!

Figure 15

| Designation | Characteristics |
|---|---|
| pRcRSV (vector) | Empty control vector |
| pRcRSV-suPAR-wt | pRcRSV plasmid encoding soluble uPAR$_{1-283}$ (encompassing domain I+II+III of uPAR) |
| pRcRSV-suPAR-del5 | pRcRSV-suPAR with a deletion of amino acid (aa) 136-180; the alternative splice site generates an exchange of isoleucine 181 to valine [I181V] |
| pRcRSV-suPAR-del4+5 | pRcRSV-suPAR with a deletion of aa 82-180 and [I181V] exchange; encompasses domain I+III of uPAR |
| pRcRSV-suPAR-DI | pRcRSV-suPAR$_{1-81}$; encodes domain I of uPAR; contains a C-terminal uPAR-unrelated extension of 16 aa (ADSQRIAFYRLLDEFF) |
| pRcRSV-GPI-uPAR-wt | pRcRSV plasmid encoding GPI-uPAR$_{1-313}$ (domain I+II+III of uPAR); posttranslationally, the GPI anchor is attached to glycine 283, thus, uPAR$_{284-313}$ is not present in the mature protein |
| pRcRSV-GPI-uPAR-del5 | pRcRSV-GPI-uPAR with a deletion of aa 136-180 and [I181V] exchange; |
| pRcRSV-GPI-uPAR-del4+5 | pRcRSV-GPI-uPAR with a deletion of aa 82-180 and [I181V] exchange; encompasses domain I+III of uPAR |
| pRcRSV-GPI-uPAR-DII+IIICP | pRcRSV-GPI-uPAR with a deletion of aa 2-82; encompasses domain II+III of uPAR and harbors the chemotactic peptide $^{88}$SRSRY$^{92}$ |
| pRcRSV-GPI-uPAR-DII+III | pRcRSV-GPI-uPAR with a deletion of aa 2-93; encompasses domain II+III of uPAR, but lacks the chemotactic peptide $^{88}$SRSRY$^{92}$ |

Figure 16
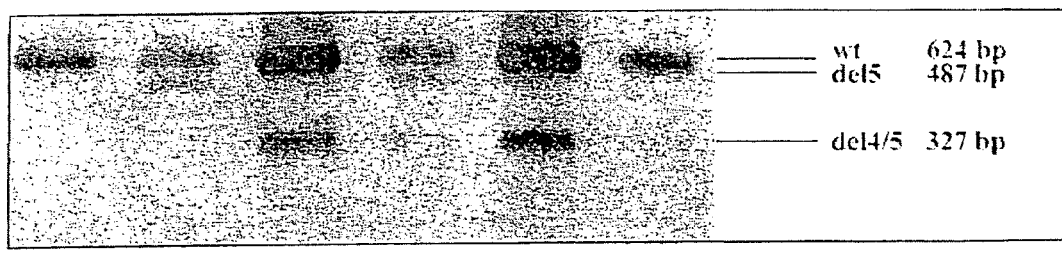
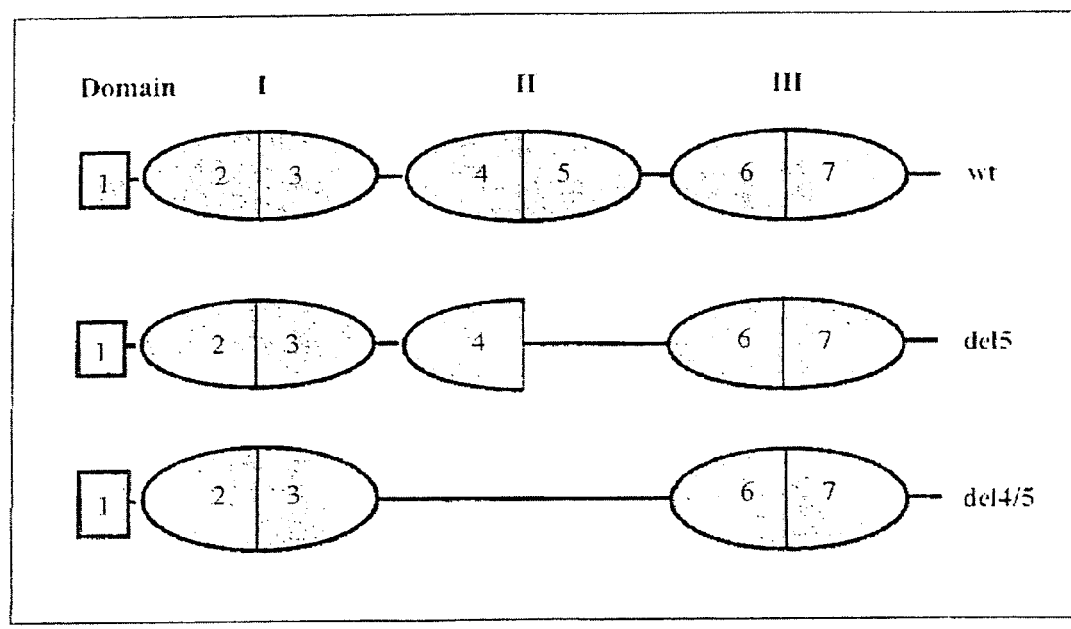
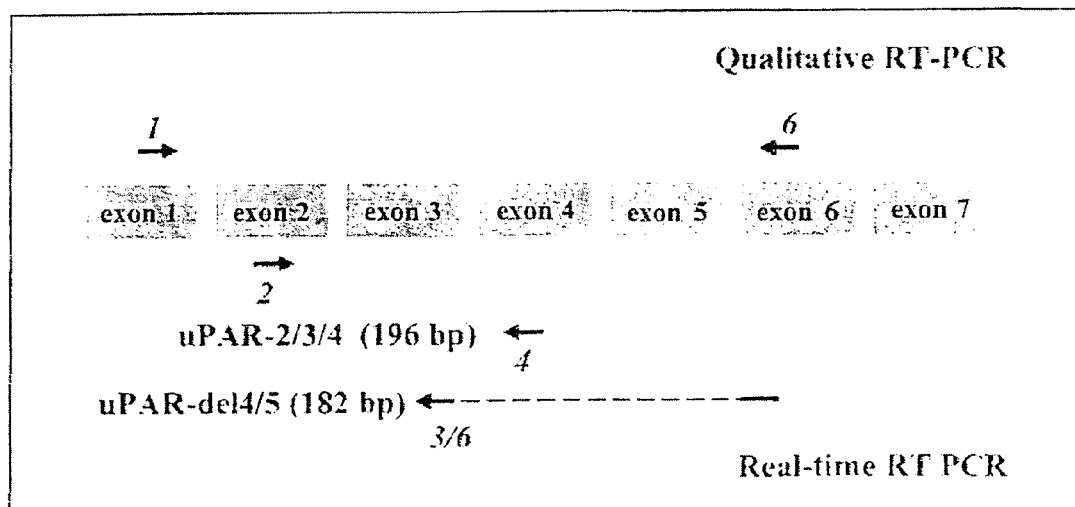

Figure 17

| cell line | type | uPAR antigen [c] ng/10[6] cells | uPAR mRNA wt | del5 | del4/5 |
|---|---|---|---|---|---|
| MCF7[a] | breast cancer | 0.33–0.01 | + | + | - |
| T47D[a] | breast cancer | 0.11–0.01 | + | n.d. | - |
| aMCF7[b] | breast cancer | 2.02–0.42 | + | + | + |
| BT549[b] | breast cancer | 1.68–0.12 | + | + | + |
| DU145 | prostate cancer | 0.60–0.11 | n.d. | + | + |
| 5637 | bladder cancer | 2.93–0.31 | n.d. | + | + |
| CHO | vector | 0.10–0.01 | - | - | - |
| CHO | DII+III | 30.0–10.2 | - | - | - |
| CHO | del5 | 7.20–1.76 | - | + | - |
| CHO | del4/5 | 12.40–4.09 | - | - | + |

[a] *epitheloid breast cancer cells*

[b] *fibroblastic breast cancer cells*

[c] *results are presented as mean of three independent experiments –SD*

Figure 20
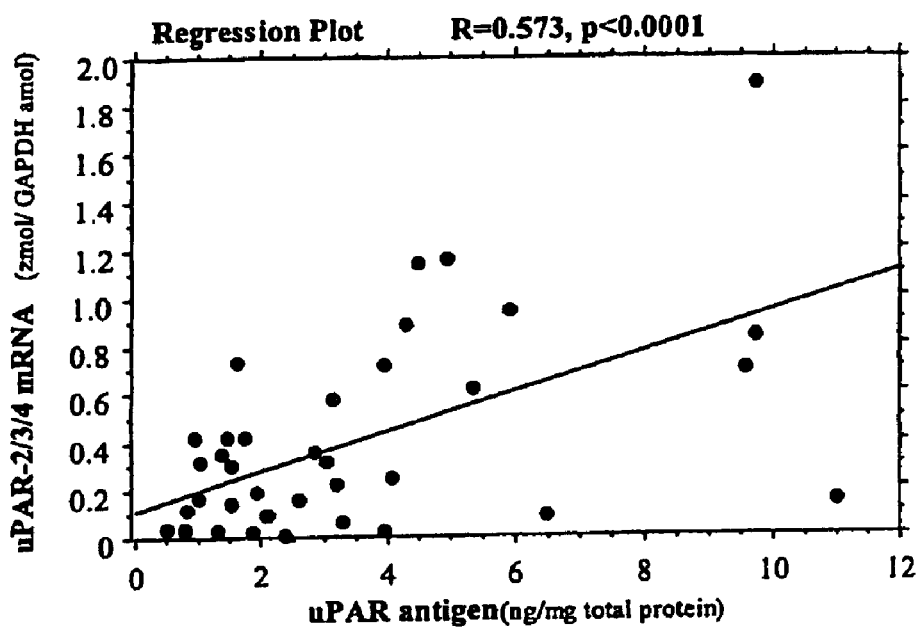
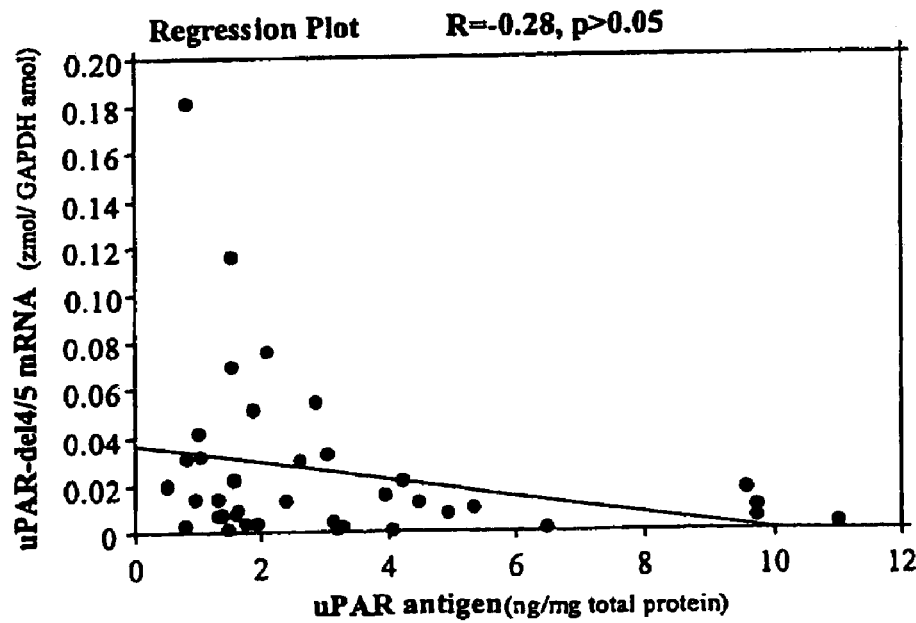

Figure 21

|  | Ratio uPAR-del4/5 - vs. uPAR-2/3/4 mRNA | | |
|---|---|---|---|
| Patients | <0.043[a] | 0.043 to 0.5 | >0.5[b] |
| total | 49 % | 26 % | 25 % |
| no disease recurrence 47 % (n=18) | 34 % | 8 % | 5 % |
| with disease recurrence 53 % (n=21) | 15 % | 18% | 20 % |

[a] *median*
[b] *in 4 cases the ratio was arbitrarily set to >1, although the detected uPAR-2/3/4 mRNA values (molecule number) was below the detection limit*

Figure 22

|  | Patients | Relapse frequency | Logrank test for DFS[a] (p) |
|---|---|---|---|
| Total No. | 43 | 25 | |
| Lymph node status | | | |
| negative | 23 | 9 | 0.0277 |
| positive | 20 | 16 | |
| Grading (Bloom-Richardson) | | | |
| I +II | 31 | 15 | 0.0133 |
| III | 12 | 10 | |
| PAI-1 antigen[b] | | | |
| < 10.4 | 21 | 9 | 0.0203 |
| ‡ 10.4 | 22 | 16 | |
| uPA antigen[b] | | | |
| < 3.45 | 21 | 7 | 0.0012 |
| ‡ 3.45 | 22 | 18 | |
| uPAR antigen[b] | | | |
| < 2.0 | 21 | 10 | n.s. |
| ‡ 2.0 | 22 | 15 | |
| uPAR-2/3/4 mRNA[c] | | | |
| < 0.222 | 21 | 14 | n.s. |
| ‡ 0.222 | 22 | 11 | |
| uPAR-del4/5 mRNA[c,d] | | | |
| < 0.0125 | 20 | 5 | 0.0004 |
| ‡ 0.0125 | 19 | 16 | |

[a] *Kaplan-Meier estimation (Mantel Cox)*

[b] *median, ng antigen / mg of total protein*

[c] *median, zmol mRNA / amol GAPDH mRNA*

[d] *in 4 cases, the level of uPAR-del4/5 mRNA was not determined due to limited RNA isolated from tumor tissue*

METHODS FOR THE DETECTION AND PROGNOSIS OF BREAST TUMORS

CROSS REFERENCE TO RELATED APPLICATION

This application is a Continutation-in-Part from PCT/EP02/03799, filed Apr. 5, 2002, which claims the benefit of DE 101 17 381.4, filed Apr. 6, 2001.

This invention relates to the production and use of specific antibodies for the detection of human tumor associated urokinase-type plasminogen activator receptor (uPAR) deletion variants in biological samples.

New perceptions of the role of the tumor-associated urokinase-receptor in tumor invasion and metastasis of solid malignant tumors are the fundamental basis for the development of new therapy strategies which are based upon tumor biology, in particular in breast and ovarian cancer. The invasive growth of tumors as well as the development of tumor metastasis are known to be multifactorial processes, among which the proteases of the plasminogen activator system, like the urokinase-type plasminogen activator (uPA) und it's inhibitor (PAI-1), play a determining role. The uPA-receptor (uPAR; CD87) takes a key position due to it's ability to focus and activate the uPA enzyme system on the cell surface. Since uPAR appears structurally in different molecular forms in tumors, it is difficult to characterize it's functional and biochemical properties.

The urokinase-receptor, uPAR, which is a heavily and heterogeneously glycosylated protein with a relative mass of 45-60 kDa is anchored via a GPI-lipid anchor in the cell membrane. In the primary structure of uPAR, three different homologue domains can be differentiated, of which each are coded by two exons of the uPAR gene. The interaction with uPA is mainly mediated by domain I (DI) of uPAR. However, further determinants for the uPA/uPAR-interaction are localized in domain II (DII) and domain III (DIII). uPAR can bind vitronectin, a protein of the extracellular matrix with high affinity by a further interaction determinant (presumably located in DII/III). After binding of uPA intracellular signal transduction can be mediated by different pathways. uPAR builds multimeric complexes with other membrane—and "second messenger"—proteins in the cell membrane of activated monocytes, which cause signal transduction, and indicates their functional cooperation.

It is known, that uPAR does not only underlie a posttranslational regulation and reversible activation because of cellular stimulation and ligand binding. Due to its structure, uPAR can appear in different molecular forms. These different forms may have different biological activities in tissue, in particular in tumor tissue. After cleavage of the glycolipid anchor by cell-associated enzymes, the soluble form of uPAR (suPAR) can be detected in body fluids of tumor patients. In addition, different glycosylation variants of uPAR were described. Stimulation of cells (e.g. by phorbolester) leads to a clear increase of the glycosylation grade of uPAR. Mild chymotrypsination cleaves the uPAR molecule between DI and DII. The resulting fragments DI and DII/III show chemotactic activity in vitro for different cell types. Only limited statements are found in the literature on the in vivo deposit of the uPAR fragments DI and DII/III, respectively. It was described, however, that a DII/III uPAR variant (by cleavage of DI) is found in some tumor cell lines and in ovarian cyst fluid of ovarian cancer. A tumor selective appearance of uPAR deletion variants is so far not known. In addition, no method exists so far which would be capable of selectively detecting uPAR deletion variants.

It was now surprisingly found that a higher expression rate of uPAR deletion mutants was found in tumor cells. Furthermore, a method is provided which is capable of characterizing tumor associated variants, in particular deletion variants of uPAR in ovarian and mammary tumors. Results produced by the use of this method can be utilized in tumor diagnostics and in particular as a parameter to judge prognosis. The method preferably comprises the use of uPAR antibodies under conditions which allow the selective determination of uPAR deletion variants, to evidence uPAR variants in biological samples, e.g. in an ELISA method. Here, preferably antibodies are used which selectively bind uPAR deletion variants. Furthermore, uPAR deletion variants are provided for therapeutic intervention and agent screening.

One embodiment of the invention relates to nucleic acids, which code for the deletion variants of the human uPAR receptor which preferably at least partially and/or essentially completely lack one or two exons of the complete sequence, for example exon 4 and/or exon 5. These nucleic acids preferably code for polypeptides which are selectively expressed in tumors and tumor cells, in particular in human mammary and ovarian tumors. "Selectively expressed" means under these circumstances, that a different expression rate is qualitatively or/and quantitatively detectable with a suitable test in tumor cells and normal cells.

FIGS. 1 (SEQ ID No. 1 and 2), 2 (SEQ ID No. 3 and 4), and 3 (SEQ ID No. 5 and 6) show the nucleotide and amino acid sequence of the preferred tumor associated uPAR deletion variants del4, del4+5, and del5. The sequence of deletion variant del5 according to FIG. 3 (SEQ ID No. 5 and 6) is already described in a public database (Genbank Accession No. U8839). However, no hint towards a tumor selective expression of this deletion variant can be found there. FIGS. 4A, 4B (middle strand: overlap SEQ ID No. 9), 5A, 5B (middle strand: overlap SEQ ID No. 10), and 6A, 6B (middle strand: overlap SEQ ID No. 11), show a comparison of the nucleotide and amino acid sequence of the deletion variants with the corresponding wild-type sequence (SEQ ID No. 7 and 8).

In addition to the nucleotide sequences in FIGS. 1-3, the complementary sequences and the sequences that in line with the genetic code commensurate to these nucleotide sequences, the present invention also comprises nucleotide sequences which hybridize with one of the aforementioned sequences, preferably with the fusion sites. Especially preferred the nucleotide sequence of this invention is double-stranded or single-stranded DNA, but it can also be RNA. Especially preferred are nucleotide sequences of this invention comprising a part of the displayed nucleotide sequences or a sequence, which has an identity of more than 80%, preferably more than 90% and in particular preferably more than 95% of the displayed nucleotide sequences or preferably an at least 18 nucleotides comprising segment of it. The grade of identity I is calculated as follows:

$$I(\text{in \%}) = \frac{N}{L} \times 100$$

whereby N is the number of identical bases between the sequence to be studied and the basic sequence and L is the length of the basic sequence.

Nucleotide sequences of this invention are preferably available from mammals and in particular from human beings, e.g. by nucleic acid amplification, e.g. by PCR. On the other hand, nucleic acids can also be generated by recombinant methods and/or by chemical synthesis.

Probes and primers of this invention, particularly uPAR specific oligonucleotides, are characterized in that they selectively recognize the uPAR deletion variant and not the native sequence, i.e. selectively hybridize with an uPAR deletion variant coding nucleic acid. They can also be used according to known methods as hybridization probes and/or amplification primers. They span preferably the deletion area, i.e. the beginning of the sequence is upstream of the beginning of the deletion and the end of the sequence is downstream of the end of the deletion.

Probes and primers are preferably equipped with markers or labeling groups. Preferred are also primer combinations which are suitable for the identification of different mRNA/cDNA species. In particular such primers are preferred which span the uPAR deletion areas in del4 or/and del5 or/and del4+5.

Further embodiments of this invention relate to polypeptides, namely uPAR deletion variants, which are coded by the above defined nucleic acids and to their use as diagnostic and therapeutic targets. These polypeptides comprise preferably the amino acid sequences of FIG. 1 for del4 (SEQ ID No. 2), FIG. 2 for del4+5 (SEQ ID No. 4), and FIG. 3 for del5 (SEQ ID No. 6).

In addition to the displayed polypeptide sequences this invention also concerns variants and fragments thereof. Among these are short amino acid segments of the displayed amino acid sequences which have a minimum length of six amino acids, particularly preferred of eight amino acids, and primary sequences of the deletion areas which are different to the complete uPAR primary sequences.

Furthermore, peptides and polypeptides of this invention can also be synthesized chemically.

The invention comprises also allelic variations or splice variations of the uPA-receptor proteins, as well as proteins produced by recombinant DNA technology, which in respect of their biological and/or immunological activity essentially correspond to the described proteins.

The polypeptides of the invention can be used in a method useful for the identification of agents, that selectively modulate the activity of an uPAR deletion variant, especially inhibit the activity of an uPAR variant.

A further embodiment of the present invention relates to a vector that contains at least one copy of the nucleic acids of this invention. This vector can be any prokaryotic or eukaryotic vector that contains the DNA-sequence of this invention, preferably together with expression signals, like promoters or further expression control sequences. The vector described in this invention is most preferably an eukaryotic vector, e.g. a vector suitable for higher cells, like a plasmid vector.

A further embodiment of the present invention concerns a cell which was transformed with a nucleic acid as described in this invention or a vector as described in this invention. The cell can be an eukaryotic as well as a prokaryotic cell. Methods for the transformation of cells with nucleic acids are common state of the art and therefore need not to be explained in detail. Examples for preferred cells are eukaryotic cells, in particular cells derived from animals and particularly preferred mammalian cells.

A further embodiment of the present invention concerns a method for the recombinant production of polypeptides of the invention comprising the steps of: providing a nucleic acid according or a vector as described above, introducing the nucleic acid or vector into a suitable host cell, culturing the host cell in a suitable medium for the purpose of polypeptide expression, and isolation of the expression product from the medium and/or the host cell. Preferably said host cell is a mammalian cell, e.g. CHO.

Further embodiments of the present invention relate to antibodies against the deletion variants of the uPAR polypeptide. Polyclonal antisera can be obtained by immunization of laboratory animals with polypeptides or fragments thereof, respectively, which are described in this invention. For the production of antibodies the peptides and/or polypeptides described in this invention are preferably coupled to carrier proteins like KLH (Keyhole Limpet Hemocyanin) or BSA (Bovine Serum Albumin).

The resulting conjugates can be used as immunogens for the immunization of laboratory animals, e.g. rabbit, chicken, guinea pig, goat, sheep, or horse. Particularly preferred for the immunization are peptides that correspond to the fusion crossover of the uPAR deletion variants. The subsequent resulting polyclonal antibodies essentially do not show any cross reactivity to native uPAR. The cross reactivity should be less than 20%, preferably less than 10% and most preferred less than 5%.

The antibodies described in this invention can also be conjugates with a labeling group and/or cytotoxic group. The labeling group can be an enzyme like alkaline phosphatase or peroxidase, a fluorescence label, as well as a radioactive labeling. Cytotoxic labeling can be radionucleotides or toxins. Antibodies of such nature could be used for diagnostic tests, in particular in mammary or ovarian cancer tissue, as well as for therapeutic purposes. For instance, using the ELISA technique, samples can be analyzed with respect to the presence of deletion variants in biological samples. Furthermore, said antibodies can be used as inhibitors of uPAR deletion variant activity.

By using the selective antibodies of the present invention it is possible to produce a test system for the prognostic evaluation of tumor tissue extracts to determine the frequency of relapse or the probability of survival of tumor patients, i.e. that by using the antibodies of this invention valuable information regarding the prognosis of tumor patients can be obtained.

Diagnostic analysis can also be carried out with specific nucleic acid probes for the detection on the nucleic acid level, in particular on the transcription level. Suitable are probes/primers of this invention for the production of a kit for the amplification of uPAR deletion variant specific mRNA, e.g. in a RT-PCR application.

Furthermore, the invention concerns a pharmaceutical composition, which is characterized by the fact that it contains nucleic acids, transformed cells, polypeptides, peptides and/or uPAR deletion variant selective antibodies as active components. Particularly preferred is the use of this pharmaceutical composition, preferably of an uPAR deletion variant specific antibody, as a therapeutic or diagnostic agent in tumor diseases such as mammary and ovarian cancer.

Furthermore, antibodies that are directed against the deletion variants of uPAR can be used for the production of a therapeutic agent, which e.g. selectively blocks the function of tumor cells. Moreover, these antibodies in form of conjugates with a cytotoxic group can be utilized to prevent growth of tumor cells or to kill the tumor cells.

Further embodiments of the present invention are antisense nucleic acids, e.g. oligonucleotides described above, which cover the fusion area of the uPAR variants and can specifically be used to block the expression of uPAR variants.

Furthermore, the invention concerns a method for the detection of tumors associated with the generation of at least one uPAR deletion variant comprising the steps of:

(a) obtaining a cDNA containing sample from a tumor to be investigated, and
(b) analysing the cDNA of said sample to determine whether alternative splicing of uPAR has occurred and at least one uPAR deletion variant has been generated, wherein the at least one uPAR deletion variant is del4, del5 and/or del4+5.

According to the invention, the step of analysing the cDNA of said sample comprises: amplifying the cDNA to obtain a quantified control amplification product comprising the nucleic acid coding for wild type uPAR or a fragment thereof and a quantified amplification product comprising the nucleic acid coding for the at least one uPAR deletion variant or a fragment thereof, if present, and determining the ratio of wild type uPAR:uPAR deletion variant by comparing the quantified amplification products. Preferably the cDNA is amplified with a first set of primers complementary to sequences contained in regions bridging the deleted sequences in uPAR deletion variants to obtain the amplification product comprising the nucleic acid coding for the at least one uPAR deletion variant or a fragment thereof, and wherein the cDNA is amplified with a second set of primers complementary to sequences contained in the wild type uPAR to obtain the control amplification product comprising the nucleic acid coding for wild type uPAR or a fragment thereof.

The amplification of the cDNA can be done by conventional amplification procedures known in the art. Preferably the amplification of the cDNA is done by real-time RT-PCR amplification. More preferably the amplification of the cDNA is done by real-time LC RT-PCR.

According to the invention, the tumor sample, which can be used in the method for the detection of tumors associated with the generation of at least one uPAR deletion variant, can be any tumor sample of any origin. It is however prefered that the tumor sample is obtained from a patient, e.g. a human being. In particular, the tumor sample is obtained from a tumor selected from the group consisting of breast, ovarian, small cell lung, and pancreatic tumors. More preferably the tumor sample is a breast tumor sample.

In a prefered embodiment of the invention the method for the detection of tumors associated with the generation of at least one uPAR deletion variant is used for providing a prognosis for tumors associated with the generation of at least one uPAR deletion variant. In this connection it is prefered that the ratio of wild type uPAR:uPAR deletion variant is greater than 0.043.

According to the invention, the term "prognosis" inter alia comprises the characterization of tumors associated with the generation of at least one uPAR deletion variant, e.g. if the tumors investigated are more invasive, are more likely to have metastasis, are more likely to have a shorter disease free survival period or have higher rates of recurrence than tumors not associated with the generation of uPAR deletion variants.

Moreover, the invention relates to a method of predicting the risk of cancer in a tumor-bearing patient comprising the steps of:
(a) obtaining a cDNA containing sample from a tumor of said patient, and
(b) analysing the cDNA of said sample to determine whether alternative splicing of uPAR has occurred and at least one uPAR deletion variant has been generated, wherein the at least one uPAR deletion variant is del4, del5 and/or del4+5, wherein patients having tumors associated with the generation of at least one uPAR deletion variant are at a higher risk to develop cancer than patients having tumors not associated with the generation of uPAR deletion variants.

According to the invention, the step of analysing the cDNA of said sample comprises: amplifying the cDNA to obtain a quantified amplification product comprising the nucleic acid coding for the at least one uPAR deletion variant or a fragment thereof, if present. Preferably the cDNA is amplified with a set of primers complementary to sequences contained in regions bridging the deleted sequences in uPAR deletion variants to obtain the amplification product comprising the nucleic acid coding for the at least one uPAR deletion variant or a fragment thereof.

The amplification of the cDNA can be done by conventional amplification procedures known in the art. Preferably, the amplification of the cDNA is done by real-time RT-PCR amplification. More preferably, the amplification of the cDNA is done by real-time LC RT-PCR.

According to the invention, the tumor sample, which can be used in the method for the detection of tumors associated with the generation of at least one uPAR deletion variant, can be any tumor sample of any origin. It is however prefered, that the tumor sample is a breast, ovarian, small cell lung, or pancreatic tumor sample.

The invention also relates to a method of providing a prognosis for a tumor-bearing patient comprising the steps of:
(a) obtaining a cDNA containing sample from a tumor of said patient,
(b) analysing the cDNA of said sample to determine whether alternative splicing of uPAR has occurred and at least one uPAR deletion variant has been generated, wherein the at least one uPAR deletion variant is del4, del5 and/or del4+5, and
(c) correlating the presence of the at least one uPAR deletion variant in the tumor of the patient with a prognosis of the patient.

According to the invention, the step of analysing the cDNA of said sample comprises: amplifying the cDNA to obtain a quantified control amplification product comprising the nucleic acid coding for wild type uPAR or a fragment thereof and a quantified amplification product comprising the nucleic acid coding for the at least one uPAR deletion variant or a fragment thereof, if present, and determining the ratio of wild type uPAR:uPAR deletion variant by comparing the quantified amplification products. Preferably the cDNA is amplified with a first set of primers complementary to sequences contained in regions bridging the deleted sequences in uPAR deletion variants to obtain the amplification product comprising the nucleic acid coding for the at least one uPAR deletion variant or a fragment thereof, and wherein the cDNA is amplified with a second set of primers complementary to sequences contained in the wild type uPAR to obtain the control amplification product comprising the nucleic acid coding for wild type uPAR or a fragment thereof.

The amplification of the cDNA can be done by conventional amplification procedures known in the art. Preferably, the amplification of the cDNA is done by real-time RT-PCR amplification. More preferably, the amplification of the cDNA is done by real-time LC RT-PCR.

According to the invention, the tumor sample, which can be used in the method for the detection of tumors associated with the generation of at least one uPAR deletion variant, can be any tumor sample of any origin. It is however prefered, that the tumor sample is a breast, ovarian, small cell lung, or pancreatic tumor sample.

In a prefered embodiment of the invention the ratio of wild type uPAR:uPAR deletion variant is greater than 0.043.

Further on, the invention is described in the following figures and examples.

FIGURES

FIG. 1 shows the nucleotide and amino acid sequence for the uPAR deletion variant del4 (nucleotide: SEQ ID No. 1 and amino acid: SEQ ID No. 2).

FIG. 2 shows the nucleotide and amino acid sequence for the uPAR deletion variant del4+5 (nucleotide: SEQ ID No. 3 and amino acid: SEQ ID No. 4).

FIG. 3 shows the nucleotide and amino acid sequence for the uPAR deletion variant del5 (nucleotide: SEQ ID No. 5 and amino acid: SEQ ID No. 6).

FIG. 4 shows a comparison between the nucleotide sequence (A: SEQ ID No. 1) and the amino acid sequence (B: SEQ ID No. 2) and the wild-type sequence (nucleotide: SEQ ID No. 7 and amino acid: SEQ ID No. 8) for the deletion variant del4.

FIG. 5 shows a comparison between the nucleotide sequence (A: SEQ ID No. 3) and the amino acid sequence (B: SEQ ID No. 4) and the wild-type sequence (nucleotide: SEQ ID No. 7 and amino acid: SEQ ID No. 8) for the deletion variant del4+5.

FIG. 6 shows a comparison between the nucleotide sequence (A: SEQ ID No. 5) and the amino acid sequence (B: SEQ ID No. 6) and the wild-type sequence (nucleotide: SEQ ID No. 7 and amino acid: SEQ ID No. 8) for the deletion variant del5.

Figure 8:
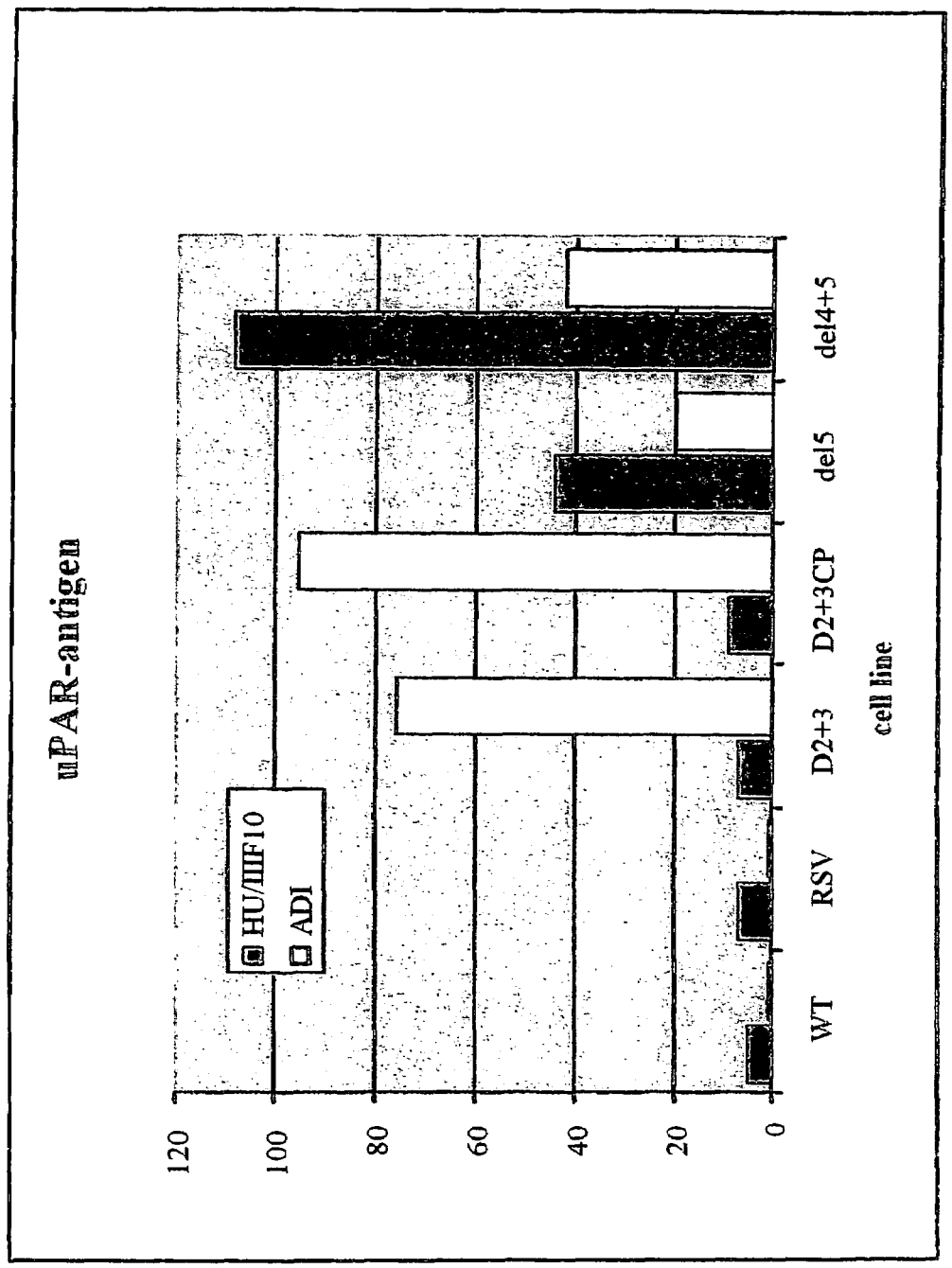

FIG. 8 shows the results of the expression of del5 and del4+5 as glycophoshoinositol-anchored variants detected by ELISA. Legend: wt=CHO cells; RSV=CHO+vector transformation; D2+3 and D2+3CP=uPAR variants without domain 1; del5=uPAR del5; del4+5=uPAR del4+5

Figure 9:
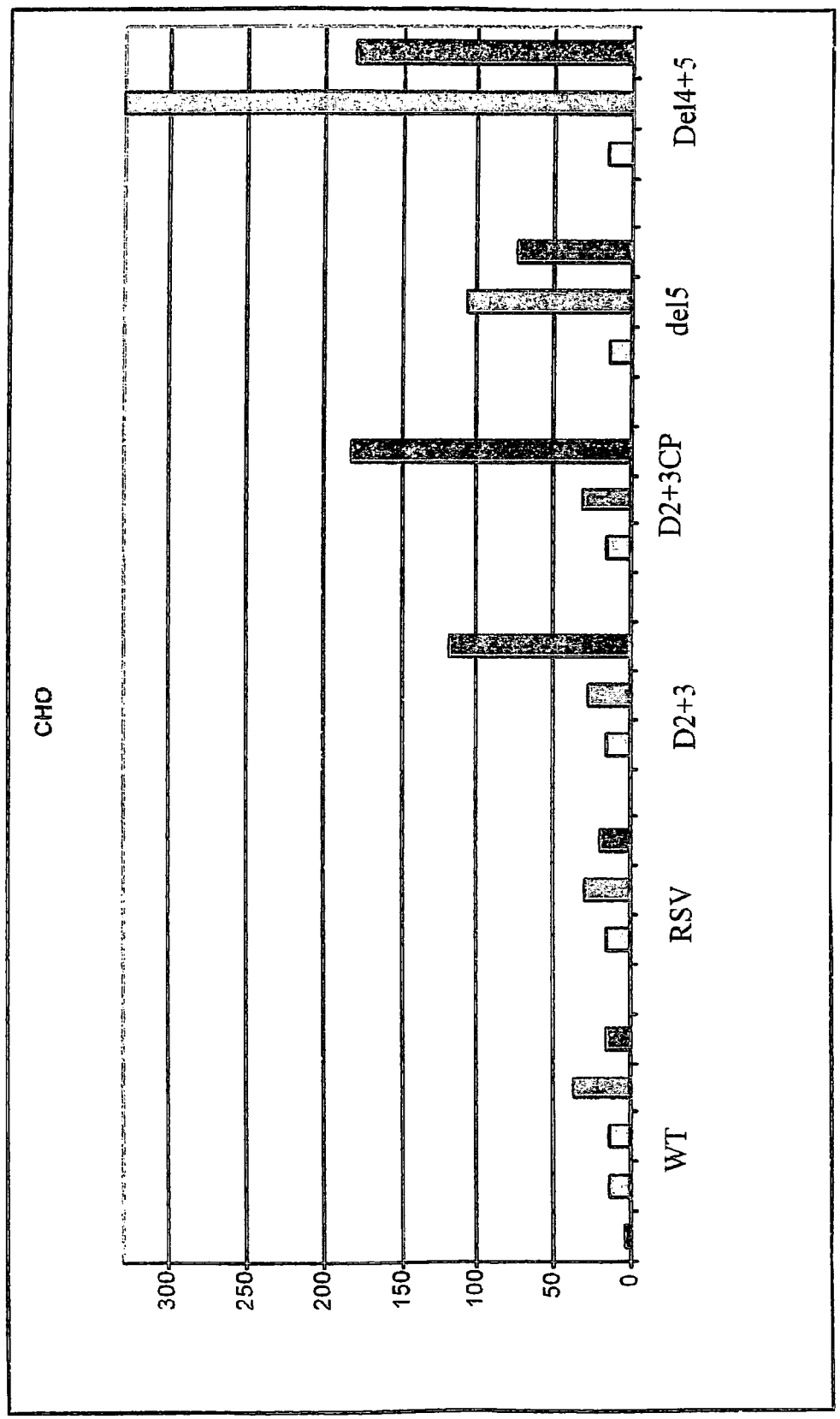

FIG. 9 shows the results of the expression of del5 and del4+5 as glycophoshoinositol-anchored variants detected by flow cytometry. Legend: gray=mouse IgG irrelevant; light blue=mAb IIIF10; blue=HD13.1

FIG. 10 shows peptides, which were selected for immunization. Identical amino acids are accentuated in yellow (uPAR del4+5: SEQ ID No. 12; uPAR del4: SEQ ID No. 13; uPAR del5: SEQ ID No. 14).

Figure 11:
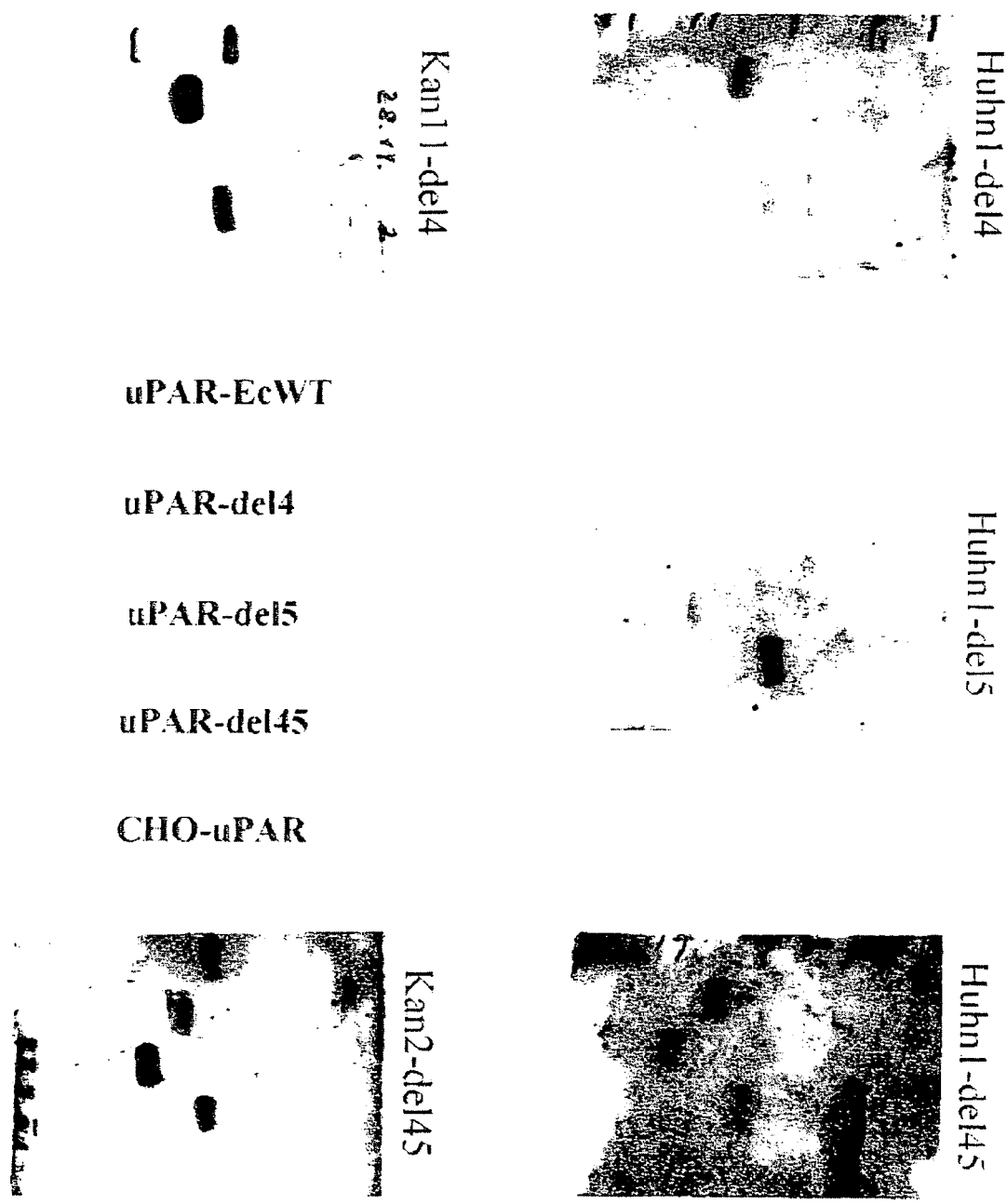

FIG. 11 shows the results of the Western-Blot analysis of the isolated peptide specific antibodies according to Example 1.3.

FIG. 12 shows a summary of the Western-Blot analysis performed according to Example 1.3.

FIG. 13 shows the results of the ELISAs performed according to Example 1.3.

Figure 14:
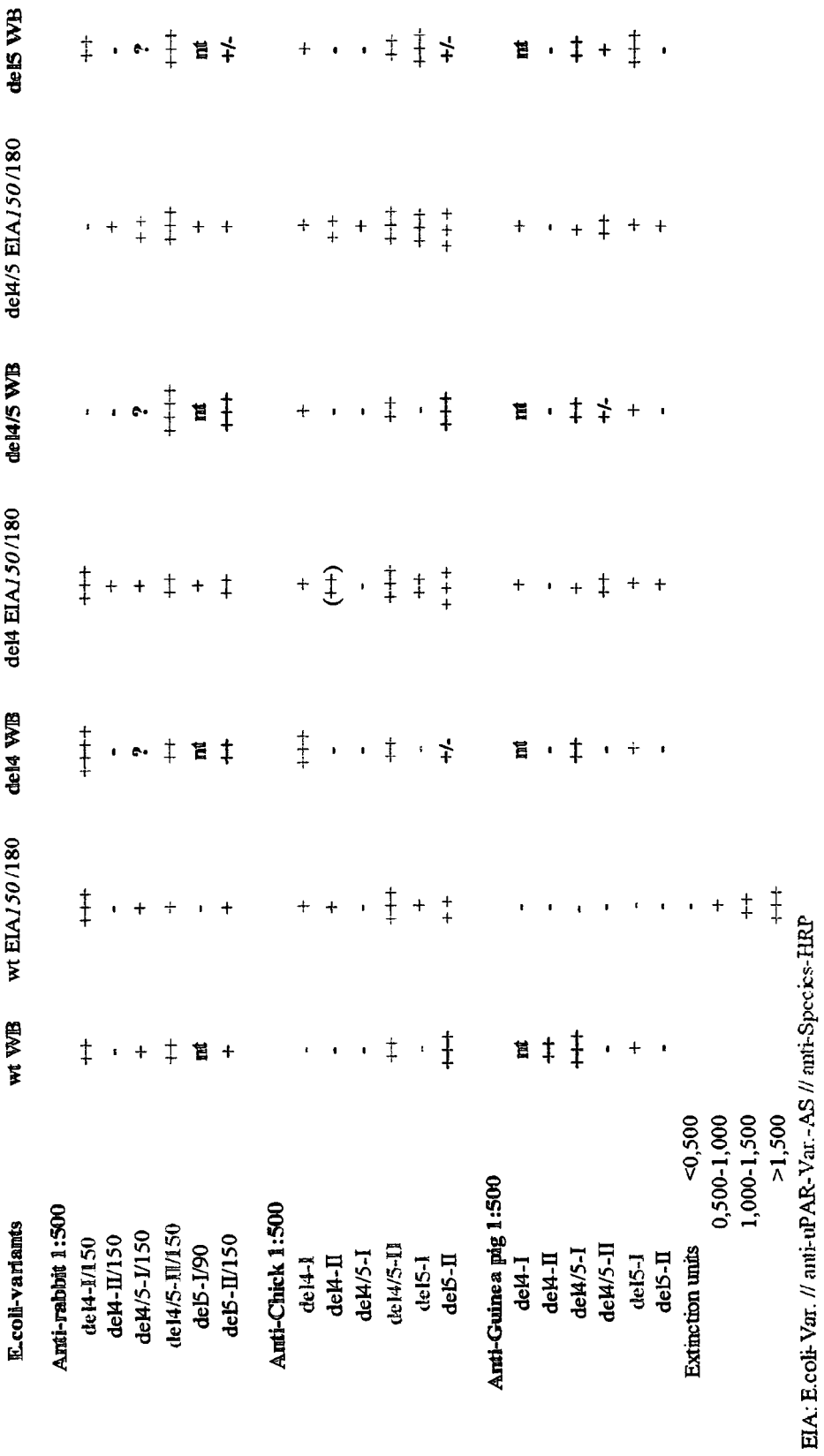

FIG. 14 shows a comparison of the Western-Blot analysis and ELISAs performed according to Example 1.3.

FIG. 15 shows various uPAR expression plasmids. In addition to the protein sequences described, all uPAR plasmids encode the native N-terminally located signal sequence of uPAR (22 amino acids) which is post-translationally clipped off during export (pRcRSV-SuPAR-DI: SEQ ID No. 15; pRcRSV-GPI-uPAR-DII+IIICP and pRcRSV-GPI-uPAR-DII+III: SEQ ID No. 16).

FIG. 16 shows the detection of uPAR mRNA splice variants.

(A) Qualitative RT-PCR analysis of non-malignant cells (keratinocytes [HaCaT], polymorphonuclear neutrophils [PMN]) and breast cancer cells (T47D, aMCF-7, MCF-7, BT549). Amplified cDNA was separated by agarose (2%) gel electrophoresis. Sequencing of the purified PCR bands confirmed the existence of uPAR-wt cDNA and uPAR variant del5 and del4+5 cDNA.

(B) Exon organization of the different splice forms and the domain structure of uPAR. Legend: wt: In wild-type uPAR, exon 1 encodes for the signal peptide sequence, each protein domain (DI, DII, DIII) is encoded by a pair of exons. del5: Variant uPAR mRNA missing exon 5 of DII. del4+5: Newly detected uPAR mRNA variant lacking exons 4 and 5 encoding DII.

(C) Primer localization for the uPAR RT-PCR. Legend: 1 and 6: forward and reverse primer, respectively, of qualitative RT-PCR, 2: forward primer of real-time PCR, 4: reverse primer of del2+3+4 PCR, 3/6: reverse primer of del4+5 PCR.

FIG. 17 shows the detection of uPAR antigen and uPAR mRNA variants in cancer cell lines and in CHO cells transfected with expression plasmids encoding GPI-linked uPAR variants. Cellular uPAR content was measured using the Imubind ADI-ELISA. The existence of uPAR mRNA variants was proved by DNA sequencing of products derived from qualitative RT-PCR. Legend: n.d.: DNA sequence not determined.

Figure 18:
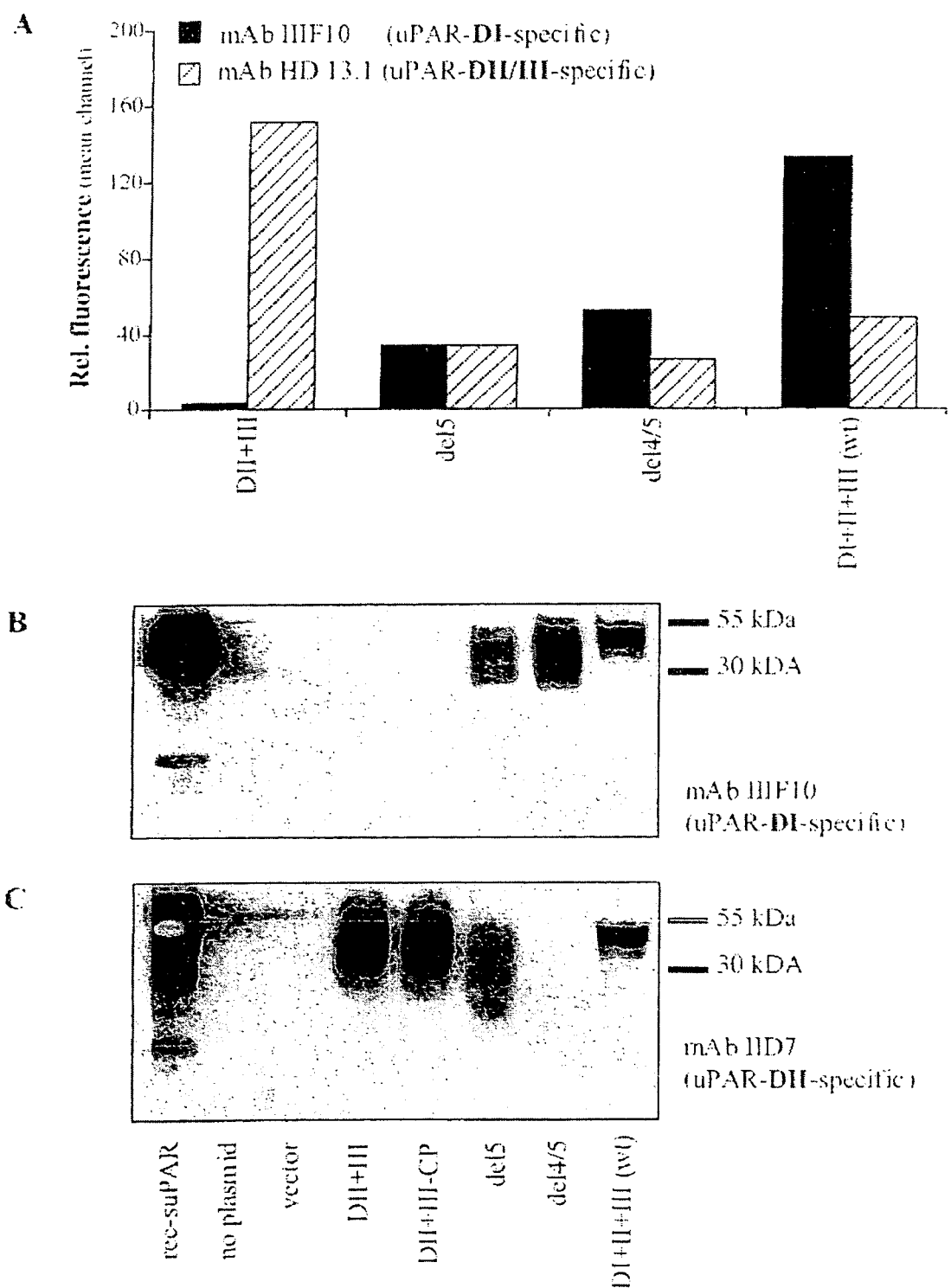

FIG. 18 shows the detection of uPAR antigen in stably transfected CHO cells with plasmids encoding GPI-linked uPAR variants.

(A) Expression of GPI-linked uPAR variants on CHO cells was detected by flow cytofluorometry using epitope-mapped mAbs against uPAR. Values are corrected for cell-associated fluorescence of vector-transfected cells. Note that the staining intensity of CHO cells expressing GPI-uPAR variants corresponds with the epitope specificity of the used mAbs against uPAR.

(B) Reaction pattern of mAbs directed against uPAR-DI and (C) against uPAR-DII in Western Blot analysis of recombinant uPAR and of lysates derived from CHO cells transfected with GPI-linked uPAR variants. Note that the DII-specific mAb IID7 (mapped epitope: aa 125-132 of domain II of uPAR) does not detect the del4+5 variant.

Figure 19:
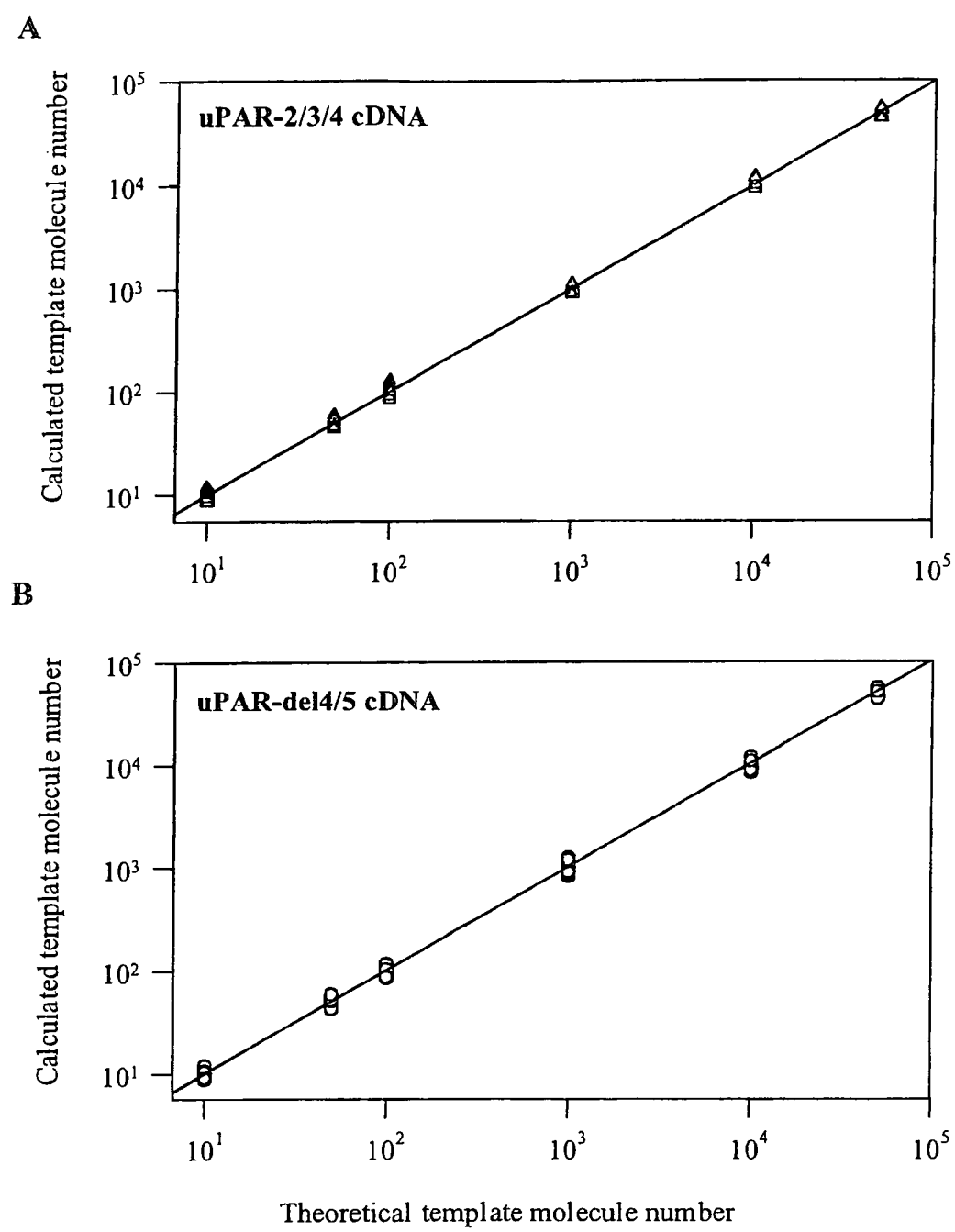

FIG. 19 shows LightCycler PCR standard curves for quantification of uPAR mRNA variants. The plots of molecule numbers detected versus theoretical molecule numbers of del2+3+4 (A) and del4+5 (B) were generated each from 14 independent PCR runs. Correlation of the values is R=0.99996 (del2+3+4) and R=1.00351 (del4+5), respectively. The coefficient of variation was 9.7% on the average for both assays.

FIG. 20 shows the relation of uPAR mRNA expression to uPAR antigen content in breast cancer tissues specimens.

(A) Regression plot of del2+3+4 mRNA analyzed by real-time LightCycler RT-PCR (normalized to GAPDH) in relation to the uPAR antigen content determined by uPAR-ELISA.

(B) Regression plot of del4+5 mRNA analyzed by real-time LightCycler RT-PCR (normalized to GAPDH) in relation to the uPAR antigen content determined by uPAR-ELISA.

FIG. 21 shows the ratio of del4+5 versus del2+3+4 mRNA values in relation to disease recurrence frequency in breast carcinomas.

FIG. 22 shows the associations of histomorphological and biochemical variables and disease-free survival (DFS) in a representative group of breast carcinoma patients. Each tumor has been histologically typed and graded. PAI-1, uPA and uPAR content of tissue extracts was measured using Imubind ADI-ELISAs. The level of uPAR mRNA variants was quantified by LightCycler RT-PCR.

Figure 23:
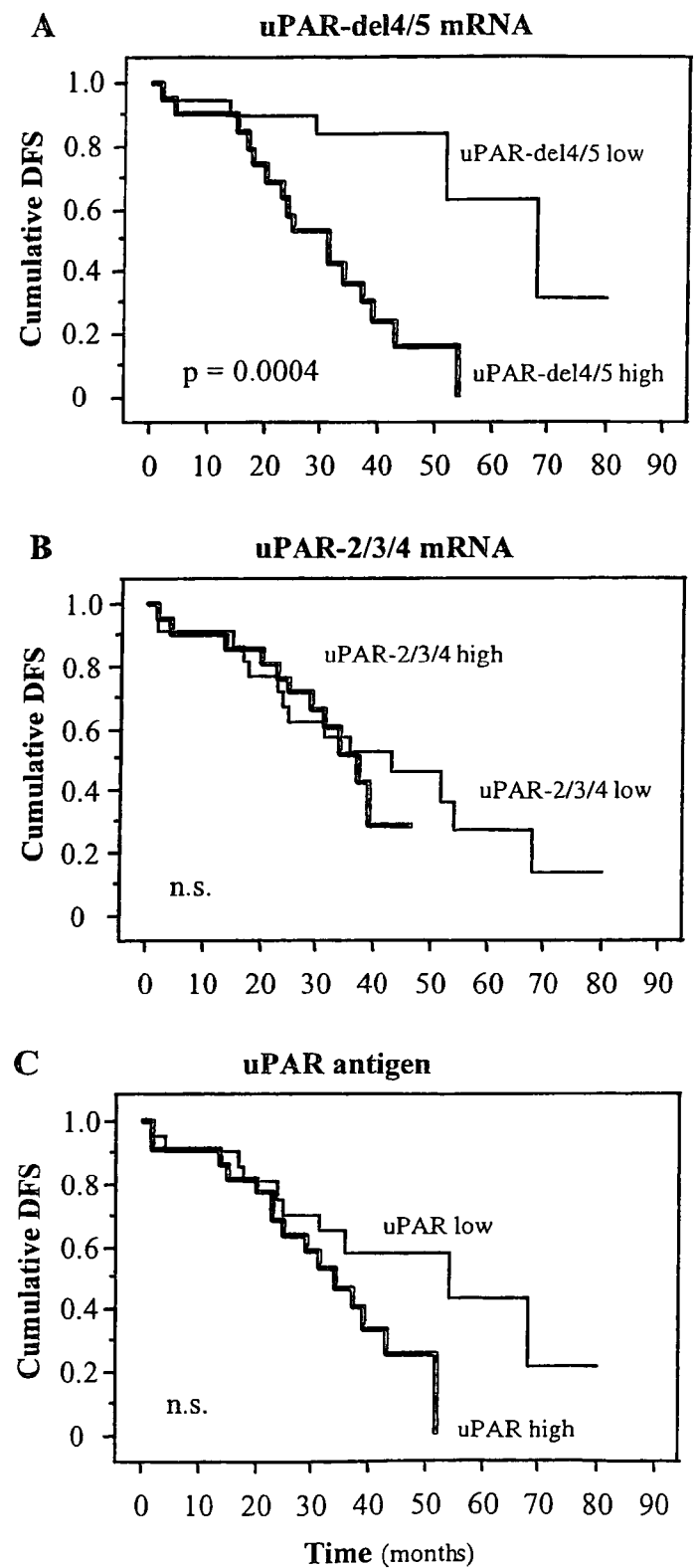

FIG. 23 shows the significance of uPA and uPAR variant expression in tumor tissue extracts of primary breast cancer. Probability of disease-free survival (DFS) in a group of 43 breast cancer patients was calculated and plotted accordingly to Kaplan-Meier statistics. Patients were grouped into low- and high-risk patients using the median value of each parameter (as summarized in FIG. 22). The level of del4+5 mRNA (A) and del2+3+4 mRNA (B) was determined quantitatively by real-time LightCycler RT-PCR. Urokinase content of tissue extracts (C) was measured by Imubind uPA-ELISA.

EXAMPLES

Example 1

In a first study, mammary tumor cell lines, non-malignant cell lines, and mammary tumor tissue were searched for alternatively spliced uPAR mRNA variants. Moreover, uPAR variant specific antibodies were produced for the analysis of uPAR variants in tumor extracts.

The study underlying Example 1 was performed according to Examples 1.1 to 1.4.

Example 1.1

Detection of mRNA Splice Variants of uPAR

To clarify whether uPAR mRNA splice variants exist in tumor cells, mRNA was isolated from mammary tumor cell lines, from non-malignant cell lines, and from mammary tumor tissue and RT-PCR was performed using specific primers for uPAR exons 1 and 6. In the non-malignant cell lines, predominately full-length uPAR-cDNA was found, whereas in mammary tumor cell lines, deletion in exon 4 (del4), in exon 5 (del5), and in exons 4+5 (del4+5), respectively, were detected. This was verified by sequencing of the amplificates. uPAR exon variants were also detected in ovarian tumor tissue.

Example 1.2

Cloning and Expression of Different uPAR Deletion Variants

Figure 7:
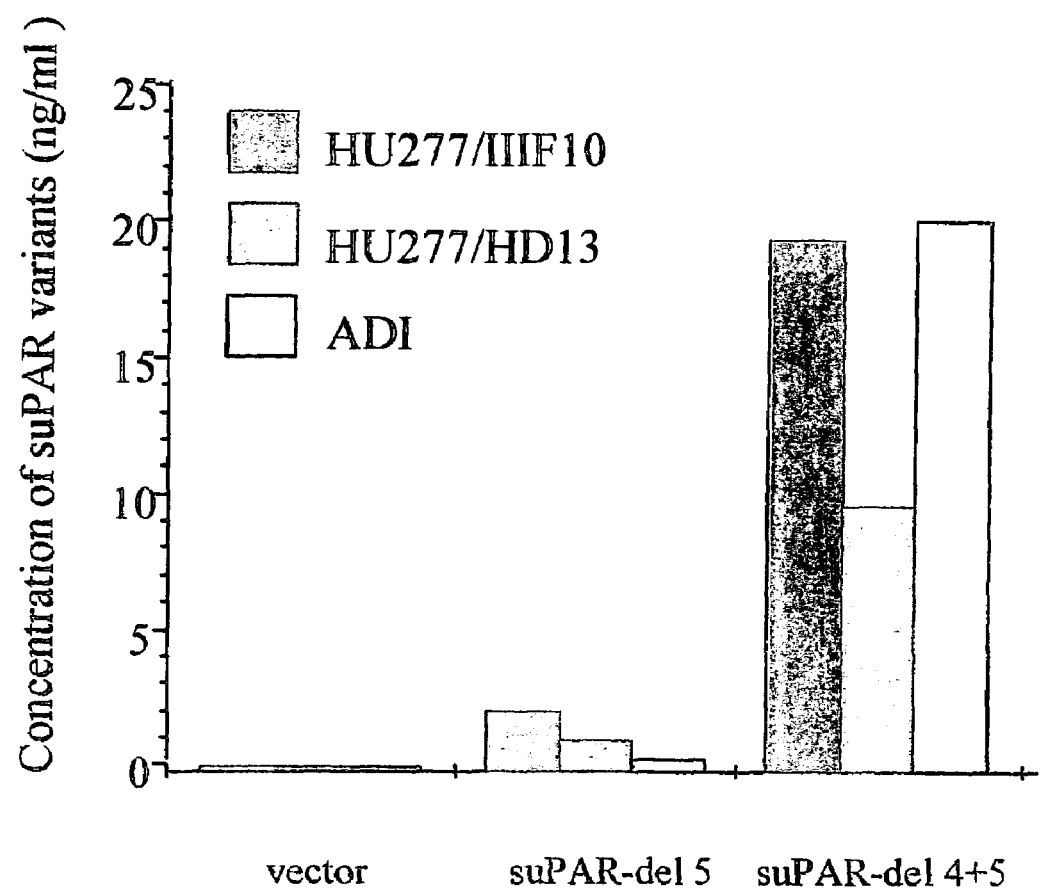
FIG. 7 shows the detection of suPAR (uPAR variants) in supernatants of CHO cells, which were transformed with uPAR variants coding plasmids. HU277/IIIF10, HU277/HD13, and ADI correspond to different ELISA systems.

Different uPAR deletion mutants (deletion-exon-4=del4, del5, del4+5) were generated, cloned, sequenced, and transfected into CHO-cells (transient transfection). As controls, transfectants with complete uPAR cDNA (D123) and cDNA for DI (D1), respectively, were used. The supernatants of the transfected CHO-cells were harvested after 72 hours and analyzed using uPAR-ELISA. All expressed uPAR-variants (suPAR) could be detected in the corresponding cell culture supernatant, vector control and culture media were negative. Whereas the uPAR variants with exon 4 deletion and the complete uPAR molecule were detected in the same manner by the ELISAs; in case of the del5 and del4+5 expression plasmid a different reaction pattern were seen. The uPAR-del5-variant was detected only partially by the HU/HD13—opposed to the HU/IIIF10-ELISA, whereas the del4+5 variant was only detected by the HU/IIIF10-ELISA. Translated proteins of all known uPAR-mRNA-splice variants are detectable with the HU/IIIF10-ELISA (FIG. 7).

uPAR del5 and uPAR del4+5 were additionally expressed in CHO cells as glycophosphoinositol (GPI)-anchored cells and the expression was confirmed by ELISA (ADI; HU/IIIF10; FIG. 8) and flow cytometry (FACS-analysis; FIG. 9). D2+3 and D2+3CP represent control variants of uPAR, which both lack domain I of the native protein. The HU/IIIF10-ELISA can not detect these variants, whereas the ADI-ELISA (American Diagnostica) can detect these variants.

Example 1.3

Production of Antibodies

Peptides (FIG. 10) are coupled to the hemocyanin of a slug (KLH, Keyhole Limpet Hemocyanin) using m-maleimido-benzoicacid-N-hydroxy-succinimidester (MBS). KLH is lightly stirred in phosphate buffer with MBS for app. 30 minutes at room temperature and excess of MBS is removed by gel filtration. Thereafter the peptide is solved in phosphate buffer and EDTA solution is added. This peptide solution is added to the concentrated MBS protein solution and is slightly shaked for four hours at room temperature. Alternatively, peptides can be coupled to bovine serum albumin (BSA) according to standard protocols.

For the immunization rabbits are normally used. The immunization of the rabbits is performed by subcutaneous injection of the coupled peptide and Freund's Adjuvant. 4 weeks after the first injection the first booster injection is applied. Thereafter, immunizations are performed in two-week intervals and after the second booster injection, always 10 days after the immunization, a blood sample is taken from the ear vein. The serum derived from the blood is used for antibody titer determination. The antibody titer is determined by an indirect ELISA procedure.

In addition to rabbits, also chicken or guinea pigs can be used to raise polyclonal antibodies according to standard procedure. Here, six animals per species (rabbit, chicken and guinea pig, respectively) were immunized with several injections to stop the immunization after 180 days to obtain serum/eggs.

The obtained sera and eggs were used to isolate the peptide specific antibodies and these were tested in Western-Blot analysis and ELISA-procedures.

For the characterization of the uPAR variants the corresponding uPAR del4, uPAR del5, uPAR del4+5, and wild-type (wt)-uPAR were produced in *E. coli* as non-glycosylated proteins (expression vector pQE30). Furthermore, glycosylated wt-uPAR from hamster-cells (CHO-uPAR) was used.

Five of 18 antibodies showed good reactivity: these were Kan1-del4; Kan2-del4+5; Huhn1-del5; Huhn1-del4 and Huhn1-del4+5. These antisera showed no reactivity with CHO-uPAR (FIGS. 11, 12, 14).

ELISA analysis confirmed the utility of the obtained antibodies also for the analysis of uPAR variants in tumor extracts (FIGS. 13, 14).

Example 1.4

Immunohistochemistry

Immunohistochemical analysis was performed using standard protocols with mammary tumor tissue slides. The antisera Kan1-del4+5; Kan2-del4+5; Kan1-del4; and Huhn2-del4+5 were used.

Huhn2-del4+5 reacts after microwave treatment also with glycosylated wt-uPAR, but also additional uPAR del4+5 staining can be seen in the tumor cell. Kan1-del4+5; Kan2-del4+5 show a similar staining pattern.

Discussion of the Results of Example 1

In the present study, novel alternatively spliced uPAR mRNA variants lacking exons 4 and/or 5 (del4, del5 and del4+5) were identified, which are present in high frequency in cultured mammary tumor cell lines but also in mammary tumor tissue. Furthermore, uPAR variant specific antibodies were produced, which can be used for the analysis of uPAR variants in tumor extracts, e.g. to obtain valuable information regarding the prognosis of tumor patients.

Example 2

In a further study, isolated non-malignant and malignant human cells as well as breast cancer tissue were searched for alternatively spliced uPAR mRNA variants. For quantification of uPAR mRNA variants, two highly sensitive real-time RT-PCR assays based on the LightCycler (LC) technology were established. Moreover, to explore the clinical significance of the expression of the uPAR mRNA variants a representative set of human breast cancer tissues was studied by real-time RT-PCR and statistical analysis were performed.

The study underlying Example 2 was performed according to Examples 2.1 to 2.4, wherein the following materials and methods were used:

Antibodies to uPAR

Monoclonal antibodies (mAbs) IIIF10 and IID7 were raised against non-glycosylated, recombinant human uPAR (amino acids 1-284 of human uPAR expressed in E. coli; EcuPAR$_{1-284}$). mAb HD13.1 was raised against glycosylated, soluble recombinant human uPAR (CHO-suPAR; amino acids 1-277 of uPAR) produced by CHO cells and lacking the glycan lipid anchor.

Cell Lines and Cell Lysates

Human breast cancer cell lines BT549, T47D, and MCF-7, prostate cancer cell line DU145 as well as bladder cancer cell line 5637 were purchased from ATCC (American Type Culture Collection, Rockville, Md.), adriamycin-resistant subline of MCF-7, aMCF-7, from the Max-Delbrück-Center for Molecular Medicine, Berlin-Buch, Germany. The human keratinocyte cell line HaCaT was obtained from the Department of Dermatology, Technical University Dresden, Germany. Cells were cultured at 37° C. in a humified atmosphere of 5% $CO_2$ and 95% air in DMEM/F-12 medium (Sigma, Deisenhofen, Germany) supplemented with 5% fetal calf serum (Gibco, Karlsruhe, Germany) and 80 ng/ml Refobacin (Merck, Darmstadt, Germany), or in UltraCulture medium (Bio-Whittaker, Walkersville, Md.) containing 2% fetal calf serum and 80 ng/ml Refobacin. Cells were harvested from monolayer cultures, resuspended in phosphate-buffered saline (PBS) (Gibco) at $5\times10^5$ cells per vial and pelleted by centrifugation at 200×g for 10 min at room temperature. Cell pellets were stored frozen at −80° C. until use. Polymorphonuclear neutrophils (PMN) were prepared from blood samples of healthy volunteers by standard Ficoll-Hypaque gradient. technique as described previously.

Cell Lysates, Tissue Extracts and ELISA for uPA, uPAR, and PAI-1

For determination of uPAR antigen in cell lysates, cells ($5\times10^5$ cells per vial) were disrupted by two freezing and thawing cycles followed by solubilization of uPAR antigen in 100 µl Triton X-100-containing sample buffer (50 mM Tris-HCl, 100 mM NaCl, 0.2% [v/v] Triton X-100, 1% [w/v] BSA, pH 7.6) for 20 min. Cell lysates were diluted 1:5 in sample buffer and then subjected to uPAR-ELISA (#893 Imubind, American Diagnostica Inc., Greenwich, Conn.). uPAR antigen levels in cell lysates are expressed as ng per $10^6$ cells.

Tumor tissue extracts were prepared from snap-frozen breast cancer tissue (stored in liquid nitrogen until use) in the presence of 1% Triton X-100. The uPA antigen content in tissue extracts was determined by uPA-ELISA (#894 Imubind, American Diagnostica Inc.) and PAI-1 antigen by PAI-1-ELISA (#821 Imubind, American Diagnostica Inc.). Protein content was determined using the Micro BCA protein assay reagent kit (Pierce, Bonn, Germany). Antigen levels are given as ng per mg of total protein.

Western Blots

Samples were separated by SDS-PAGE on 4-12% gels (Novex, Offenbach, Germany) under reducing conditions and transferred to nitrocellulose membranes (Schleicher and Schuell, Dassel, Germany) by semi-dry blotting. After blocking, the blots were incubated with mAbs IIIF10 or IID7, and antigen-bound mAbs were detected using peroxidase-conjugated rabbit anti-mouse IgG (DAKO, Hamburg, Germany) and SuperSignal chemiluminescent substrate (Pierce, Bonn, Germany).

Flow Cytofluorometric Analysis

In order to investigate expression of cell-associated uPAR variants, stably transfected CHO cells harboring the pRcRSV-GPI-plasmids or the vector control were incubated with epitope-mapped monoclonal antibodies ($2.5\times10^5$ cells in PBS/1% BSA; 2 µg of mAb for 30 min at room temperature; 250 µl total volume). Antibodies to uPAR used were mAb IIIF10 (directed to a linear epitope on domain I of uPAR, aa 52-60) and mAb HD13.1 (directed to a conformational epitope on domain II+III of uPAR). After washing steps with PBS/1% BSA, uPAR-bound antibodies were probed with Alexa Fluor 488-labeled rabbit anti-mouse IgG (MoBiTec, Göttingen, Germany) and cell-associated fluorescence determined by flow cytofluorometry (FACScan, Becton/Dickinson, Heidelberg, Germany).

Cloning of Expression Plasmids Encoding Splice Variants of uPAR

Cloning of pRcRSV-derived expression plasmids encoding either full length cell membrane-linked uPAR (GPI-uPAR) or a soluble form of uPAR (spanning amino acids 1-283) was performed. Both plasmids served as templates in reverse long range PCR (High Fidelity Expand PCR, Roche Diagnostics, Penzberg, Germany) for deletion of the DNA sequence encoding either exon 5, exon 4 and 5, domain I of uPAR, or domain II+III of uPAR (FIG. 15). Altered cDNA-inserts were verified by sequencing.

Stable Transfection of Chinese Hamster Ovary (CHO) Cells

CHO cells were transfected in the presence of Lipofectin™ (Gibco) with expression plasmids encoding soluble or GPI-linked wild-type uPAR, uPAR variants, or the empty vector (serving as a control). Transfected CHO cells were isolated upon G418 (geneticin) selection. In each case, expression of the recombinant uPAR-derived proteins was verified by ELISA, Western blot analysis, and—in the case of the GPI-linked variants—by flow cytofluorometry.

Qualitative RT-PCR for uPAR

Cellular mRNA was isolated using the MICRO FAST TRACK™ kit (Invitrogen, Karlsruhe, Germany) and cDNA synthesized using the cDNA-CYCLE™ kit (Invitrogen, Karlsruhe, Germany). PCR was performed in a master mix containing 1× PCR buffer (PE/Applied Biosystems, Forster City, Calif.), 2 mM of each desoxyribonucleotide triphoshate (Stratagene, LaJolla, Calif.), 2 µM of uPAR-specific primers for uPAR-exons 1 and 6 (SEQ ID No. 17: forward: CTCCA-CACCTGCGTCCCA, SEQ ID No. 18: reverse: CTTG-CAGCTGTAACACTG; Metabion, Martinsried, Germany) (FIG. 16), 1.0 U AMPLITAQ GOLD™ DNA polymerase (PE/Applied Biosystems), and 2 µl cDNA in a total volume of 50 µl. The amplification profile consisted of denaturation at 94° C. for 1 min, annealing at 49° C. for 45 sec, and primer extension at 72° C. for 45 sec in a 30-cycle reaction. Twenty µl of the PCR products were separated electrophoretically in 4-12% TBE-PAGE (Novex), stained with SYBR Green (Biozym Diagnostica GmbH, Hess. Oldendorf, Germany), and analyzed with the Fluor-S MultiImager (BioRad, München, Germany) using the Multi-Analyst PC software (BioRad, München, Germany). As an internal control, glyceraldehyde-3-phosphate dehydrogenase (GAPDH) was co-amplified. Amplified cDNA was separated by agarose gel electrophoresis (2%) and visible PCR products were sequenced.

Real-time Amplification of del2+3+4, del4+5 and the Reference Gene GAPDH

Based on the LIGHTCYCLER technology (Roche, Mannheim, Germany), real-time RT-PCR assays were established in order to quantify expression of uPAR mRNA variants and of the reference gene GAPDH. Specific PCR products were quantified by the detection of fluorescence signals of site-specific hybridization probes (assays for uPAR mRNA variants) or of the intercalating dye SYBR Green (assay for GAPDH mRNA).

Total cellular RNA was isolated using the Invisorb Spin Cell-RNA Mini-kit (Invitek, Berlin, Germany) and cDNA was synthesized using the cDNA-Cycle™ kit (Invitrogen). The PCR assays were performed using 2 µl of a 1:10 dilution of the respective cDNA products. Reactions were performed using ready-to-go PCR kits (LC FastStart DNA Master Hybridization Probes, Roche, for uPAR; QuantiTect SYBR Green PCR Kit, QIAGEN, Hilden, Germany, for GAPDH). All HPLC-purified primers were purchased from TibMolbiol (Berlin, Germany). Concentration of primers and probes ranged between 0.2 and 0.5 µM, $Mg^{2+}$ was applied at a final concentration of 2.5 mM (GAPDH) or of 3 and 4 mM (uPAR-assays), respectively.

For amplification of both uPAR cDNA types (mRNA encompassing exons 2, 3, and 4 [del2+3+4 or uPAR-2/3/4]; cDNA encompassing exons 2, 3, and 6 and lacking exon 4 and 5 [del4+5 or uPAR-4/5]), separate PCR reactions applying the same forward primer targeted to exon 2 (5'-GACCTCT-GCTGCAGGACCACGAT-3': SEQ ID No. 19), but different reverse primers were used. For the del2+3+4 cDNA, a primer targeted to exon 4 (AGGTAACGGCTCCGGGAAT: SEQ ID No. 20) was designed to obtain a fragment length shorter than 200 bp (FIG. 16), which allows efficient PCR performance on the LC. Using this primer set, fragments either from the uPAR-wt and/or from the del5 variants are amplified. For del4+5 cDNA, a primer overlapping the expected exon 3-6 boundary (5'-TTTCMGCTCCAGGACAGAGTT-3': SEQ ID No. 21) was used. In both assays identical hybridization probes (uPAR-fluorescein-labeled 5'-GGTA-CAGCTTTTCTCCACCAG-CTCCA-3': SEQ ID No. 22) and uPAR-LC640 5'-CTCTTCTCCTTCTTCCCA-CAAGCG-3': SEQ ID No. 23) located in exon 3 were used. Amplification of GAPDH was performed using the sense primer (5'-TGGTCACCAGGGCTGCTTTTA-3': SEQ ID No. 24) and antisense primer (5'-TCCTGGAAGATG-GT-GATGGGATTT-3': SEQ ID No. 25).

The specific PCR fragments (196 bp, 182 bp, and 187 bp for del2+3+4, del4+5, and GAPDH, respectively) were amplified as follows: pre-denaturation 10 min at 95° C., 40 cycles of denaturation (10 sec at 95° C.; for GAPDH 15 sec at 95° C.), annealing for 15 sec at 66° C. (del2+3+4), 15 sec at 63° C. (del4+5) or 20 sec at 60° C. (GAPDH), and elongation for 10 sec at 72° C.

The PCR assays were carried out at least twice in independent runs for each cDNA sample and the mean values were used for further calculations. All measurements were performed with aliquots of the same cDNA dilutions within short time periods to guarantee standardized and comparable conditions. Positive template detection was defined for a detection of at least 2 template molecules in two independent PCR reactions of the same cDNA specimens. Positive controls (cDNA from prostate cancer cell line DU145 expressing both types of uPAR mRNA, del2+3+4 and del4+5) as well as negative controls (without template) were measured in each of the PCR runs.

The mRNA copy number of a single marker was calculated in relation to the amplification product amounts of external standards. LC capillaries were coated with $10^1$ to $10^6$ template molecules per capillary of del2+3+4, del4+5 or GAPDH fragments. The transcript amounts were calculated using the fit point mode of the LC-software version 3.1 (Roche), keeping the noiseband constantly in all PCR runs for the respective marker. In the GAPDH assay based on SYBR Green, melting curve analysis was performed to confirm the specificity of the amplification product (data not shown). Specific transcript quantities (zmol) were normalized to the transcript amounts of the reference gene GAPDH (amol) within the same cDNA sample. The relative mRNA expression ratio (zmol uPAR/amol GAPDH) was used for all calculations and statistical analyses.

Patients

Tumor tissue samples from 43 patients with histologically verified primary breast carcinoma were included in this study. The representative set of tumor patients was selected at random from a greater cohort of well-characterized breast cancer patients with long-term follow-up. Locoregional treatment of patients consisted of modified radical mastectomy or breast conserving surgery with auxiliary lymph node dissection and subsequent breast irradiation. Adjuvant systemic treatment was administered according to standard recommendations (nodal negative patients included in the study were not treated adjuvantly). The patients' age ranged from 38 to 88 years (mean age 62 years). Median time of follow-up of patients still alive at time of analysis was 38 months (range: 4 to 80 months). During that time, 25 patients had relapsed.

Statistical Analysis

The association of histomorphological parameters, uPA-, uPAR- and PAI-1-antigen as well as uPAR mRNA variants with disease-free survival (DFS) was analyzed by Kaplan and Meier estimation using the log rank regression model (Mantel-Cox). As cut-off points for discriminating low-risk and high-risk patients, the median value of each parameter was used. Calculations were performed using the StatView statistical package (SAS Institute, Cary, N.C.). All tests were performed at a significance level of $\alpha(p)<0.05$.

Example 2.1

Detection of uPAR mRNA Splice Variants in Non-malignant and Cancer Cells

After RT-PCR amplification of uPAR mRNA with exon 1- and exon 6-directed primers, two smaller fragments in addition to the expected 624 bp uPAR-wt fragment were observed in 4 of the 6 cancer cell lines examined (FIG. 16). In non-malignant cells, predominantly one amplification product was found corresponding to uPAR-wt RNA (FIG. 16 and FIG. 17). In fact, the determination of the DNA sequence revealed that the sequence of the 624 bp fragment was identical to that reported for the uPAR-wt mRNA. The two additional fragments also matched the sequence of the uPAR mRNA, except that complete exons were deleted (FIG. 16). Specifically, the 487 bp band lacked exon 5 (del5). The 327 bp band (found in aMCF-7 and BT549 and verified by sequencing) was missing both exon 4 and exon 5 (del4+5) (FIG. 16). The latter result revealed the existence of the alternatively spliced variant del4+5 of uPAR mRNA, which is detectable above all in cancer cells (FIG. 17).

Example 2.2

Detection of uPAR Antigen in CHO Cells Transfected with Plasmids Encoding uPAR Variants To elucidate whether alternatively spliced uPAR mRNA may be translated and posttranslationally processed, expression plasmids encoding wt-uPAR (DI+II+III) and various uPAR variants including uPAR-DII+III, del5 and del4+5 in a GPI-linked form were generated and stably transfected into CHO cells (FIG. 15). By ELISA, flow cytofluorometry, and Western blot analysis, synthesis and secretion of wt-uPAR and the uPAR variants were demonstrated in these cells. When lysates of the transfected cells were analyzed by the use of the Imubind uPAR-ELISA (American Diagnostica. Inc.), a increased absorbance in samples derived from CHO-DII+III, CHO-del5 as well as CHO-del4+5 cells compared to the vector control was observed, which corresponds to a certain uPAR content concerning the standard curve of the test (FIG. 17). For flow cytofluorometric analysis, two different mAbs against uPAR were used, which are directed to different epitopes on DI (mAb IIIF10) and on DII/III (mAb HD13.1) domains of uPAR, respectively (FIG. 18A). With both mAbs, a distinct cell surface-associated reaction was observed with CHO cells transfected with GPI-linked uPAR-wt, the del5 as well as del4+5 plasmid variants (but not with the vector control), strongly indicating that the GPI-linked splice variants are presented at the cell surface. The DI-specific mAb IIIF10 (mapped epitope aa 52-60), as expected, did not bind to CHO-DII+III cells, which emphasizes the specificity of the analysis. In line with this, the DII-specific mAb IID7 but not the mAb IIIF10 reacted with lysates of CHO cells transfected with GPI-uPAR-DII+III plasmids (with and without the chemotactic peptide $^{88}$SRSRY$^{92}$ (SEQ ID No. 16); FIG. 15) in Western blot analysis (FIGS. 18B and C). Whereas both mAbs bound to lysates of GPI-del5 (deletion of aa 136-180) transfected CHO cells, the DII-specific mAb IID7 (mapped epitope aa 125-132) did not react with the lysates of CHO-del4+5 cells transfected with an uPAR plasmid lacking the DII-encoding exons (deletion of aa 82-180). The rather broad bands in Western blot analysis as well as the increase of the apparent molecular weight of the various uPAR variants strongly indicate that these proteins—similarly as wt-uPAR—are glycosylated in CHO cells (FIG. 18B and C).

Furthermore, soluble forms of uPAR-encoding plasmids were also expressed in CHO cells lacking either exon 5 or both exons 4 and 5 (FIG. 15). By ELISA and Western blot analyses, synthesis and secretion of wild-type uPAR and both uPAR variants were again confirmed in supernatants, whereas supernatants of vector-transfected control cells did not contain any detectable human uPAR antigen (data not shown).

Example 2.3

Specificity and Sensitivity of Real-time LC RT-PCR Assays for uPAR Variants

For quantification of del2+3+4 mRNA (encompassing exons 2, 3, and 4) and del4+5 mRNA (encompassing exons 2, 3, and 6 and lacking exons 4 and 5, respectively) two highly sensitive real-time RT-PCR assays applying the LIGHTCY-CLER technology were established. The concentration of standard DNA for capillary coating in this system was exactly determined by HPLC calibration. This clearly improved the sensitivity and the reproducibility of the assay (CV<10%; FIG. 19).

In dilution experiments using different amounts of external DNA standards ($10^1$ to $10^5$ template molecules of both standards), the false-positive detection rate of the del4+5 assay caused by mispriming of exon 3/6 specific reverse primer to the exon 3 terminus of del2+3+4 cDNA was calculated. Data from two independent series of experiments indicate that less than 0.5% of the fluorescence signals detected in the del4+5 PCR are originating from exon 4- or exon 5-containing templates. In contrast, applying the del2+3+4 assay, no target sequence in the deleted transcript template exists. As expected, no illegitime amplification products were detected (data not shown).

Example 2.4

Expression of uPAR Variants in Primary Breast Cancer and its Correlation with Disease-free Survival To determine del2+3+4 as well as del4+5 mRNA expression in breast carcinoma, real-time LC RT-PCR assays were performed using total RNA prepared from tumor tissue samples of 43 patients afflicted with primary breast cancer. Using the above described detection limit, del2+3+4 and del4+5 mRNA were found in 91% and 97% of the tissue samples investigated, respectively. The median transcript ratios were calculated as 0.222 zmol del2+3+4 per amol GAPDH and as 0.0125 zmol del4+5 per amol GAPDH. As shown by regression analysis, del2+3+4 mRNA levels of tumor samples correlated significantly to the respective uPAR antigen content ($R=0.573$, $p<0.0001$). In contrast, no correlation between del4+5 mRNA and uPAR antigen levels was found (FIG. 20). In line with this, there was no correlation between del2+3+4 and del4+5 mRNA expression (data not shown) indicating that the del4+5 splice variant is independently generated from uPAR mRNA variants covering exon 4 (i.e. uPAR-wt and del5). In about 50% of the analyzed tumors the ratios of del4+5 versus del2+3+4 mRNA were greater than 0.043 (median), in 25% of the tumors the value was greater than 0.5. Strikingly, high del4+5 versus del2+3+4 ratios were associated with high relapse frequency (FIG. 21).

By univariate Cox regression analysis, an elevated level of del4+5 mRNA in tumor tissue (>0.0125 zmol/amol GAPDH) significantly correlated with an increased frequency of disease recurrence and thus with poor prognosis ($p=0.0004$) was found, whereas uPAR antigen and del2+3+4 mRNA did not (FIGS. 22 and 23). A strong association between lymph node status of the patients and del4+5 mRNA expression in the tumors could not be found, since 6 out of 20 patients with low and 8 out of 19 patients with high del4+5 expression were nodal positive. In addition, FIG. 22 depicts the relationships between relapse frequency and histological grade as well as clinically relevant prognostic markers such as uPA and PAI-1.

As expected, there was a significant association between lymph node status, histological grade, uPA- as well as PAI-1-antigen levels and DFS indicating that the randomly selected and analyzed set of tumor specimens was representative. The Kaplan-Meier survival curves (FIG. 23) also demonstrate that patients with high levels of del4+5 mRNA in tumors have substantially shorter DFS.

Discussion of the Results of Example 2

In the present study, the alternatively spliced uPAR mRNA variant lacking both exons 4 and 5 (del4+5) is described, which is present in high frequency in cultured malignant human cells but also in breast cancer tissue. By expression of both soluble and GPI-linked variants of del4+5 in CHO cells, it could be demonstrated that this splice variant lacking both exons 4 and 5 (coding for complete DII) is translated and post-translationally processed. Thus, secreted soluble del4+5 protein in supernatants as well as GPI-anchored del4+5 protein on the cell surface expressed by stably transfected CHO cells could be detected. In Western blot analysis using a DI-specific antibody, it could be observed that not only the wt-uPAR (DI+II+III), but also the expressed splice variants del5 and del4+5 gave the expected broad band characteristics of human highly glycosylated uPAR. In addition, a DII-specific antibody (mapped epitope: aa 125-132) binds to both DII-containing uPAR and del5 protein variants, but did not recognize the del4+5 protein. With regard to these results, it is likely that at least in tumor cells and tissue extracts, in which a rather high del4+5 expression could be found, an uPAR protein variant lacking DII is produced.

In ELISA, applying the Imubind uPAR-ELISA, an increased absorbance in both supernatants and lysates of stably transfected CHO-DII+III, CHO-del5, and CHO-del4+5 cells compared to the vector control could be found, which corresponds to a signal indicating a certain uPAR content in relation to a standard curve achieved with soluble recombinant wt-uPAR. This indicates that the commercially available uPAR ELISA may not only detect wt-uPAR but also uPAR protein variants. The measured uPAR protein content in lysates of cancer cells by this ELISA may, therefore, be a result of the protein expression of different uPAR mRNA variants, which are present in these cells. Thus, these findings stress the need of well characterized antibodies as such described in the present invention and ELISA-formats in setting up detection and quantification of uPAR antigen in tumor samples. In addition, it is tempting to speculate that tumor cells produce additional forms or variants of uPAR, which may contribute to the at least in part conflicting results concerning the prognostic relevance of uPAR in cancer patients.

The presence of more than one mRNA form derived from the same gene is a common observation for a growing number of proteins. These forms may result from alternative splicing, retained intronic segments or the utilization of alternative transcription initiation or polyadenylation sites. Variation of the splicing process occurs during tumor progression and may play a major role in tumorigenesis. Especially for many cancer-associated genes—such as CD44, WT-1, survivin, mdm2, MUC-1, and VEGF—a broad spectrum of alternatively and/or aberrantly splice variants with different and often oncogenic functions have been identified. However, only a few of the described mRNA splice variants are both expressed in a biological relevant concentration and detectable in a significant amount. Furthermore, often it is unknown whether these variant transcripts are translated into protein. Characterization of splice variants of a gene may still be of importance. In addition to any biological role, such variants may have the potential of being useful diagnostic markers. For quantification of uPAR mRNA variants encompassing exons 2 to 4 (del2+3+4) and encompassing exons 2, 3, and 6 (del4+5), respectively, two highly sensitive real-time RT-PCR assays based on LIGHTCYCLER technology were established. Analysis of its expression in breast cancer tissues as shown in the present study, or in other cancer tissues (unpublished observation), indicates that the mRNA variant del4+5 is expressed frequently and independently of uPAR variants covering exon 4 (i.e. uPAR-wt and del5). In about 25% of the analyzed breast carcinomas, the mRNA expression ratio of del4+5 in relation to del2+3+4 was greater than 0.5 indicating that the del4+5 mRNA splice variant could be of physiological significance. In addition, it was demonstrated—in this small but representative set of breast cancer specimens—that high del4+5 mRNA levels are significantly associated with a short disease-free survival of the patients, whereas uPAR antigen and del2+3+4 mRNA did not. It is tempting to speculate that the weak prognostic impact of uPAR antigen content of tumor tissue extracts or cytosols in comparison to the impact of other components of the plasminogen system such as uPA and PAI-1 is due to a masking of the levels of prognostic relevant uPAR variants by other uPAR forms. The preliminary observation that del4+5 protein expressed in CHO cells does not interact with uPA raises the questions, if there are any other interaction partners and if there is an uPA-independent tumorbiological role of this cell surface-associated receptor variant lacking DII.

Taken together, the results of Example 2 suggest that the detection of del4+5 mRNA may serve as a novel prognostic marker at least in breast cancer and possibly also in other malignant tumors. Nevertheless, these data have to be validated in greater cohorts of cancer patients. In addition, the transfected CHO cells which selectively express the tumor-associated splice variant of uPAR on their surface can be used to analyze the characteristics of this variant concerning interaction with uPA, integrins, and extracellular matrix proteins such as vitronectin.

The invention claimed is:

1. A method for the detection of a breast tumors associated with the generation of at least one uPAR deletion variant comprising the steps of:
   (a) obtaining a cDNA containing sample from a breast tumor to be investigated, and
   (b) analyzing the cDNA of said sample to determine whether alternative splicing of uPAR has occurred and at least one uPAR deletion variant has been generated, wherein the at least one uPAR deletion variant is del4+5, wherein the tumor sample is obtained from a human patient, and
      wherein the presence of the at least one uPAR deletion variant in said tumor indicates the presence of a tumor associated with the generation of at least one uPAR deletion variant.

2. The method according to claim 1, wherein the step of analyzing the cDNA of said sample comprises: amplifying the cDNA to obtain a quantified control amplification product comprising the nucleic acid coding for wild type uPAR and a quantified amplification product comprising the nucleic acid coding for the at least one uPAR deletion variant, and determining the ratio of wild type uPAR:uPAR deletion variant by comparing the quantified amplification products.

3. The method according to claim 2, wherein the amplification of the cDNA is done by real-time RT-PCR amplification.

4. The method according to claim 2, wherein the ratio of wild type uPAR:uPAR deletion variant is greater than 0.043.

5. The method according to claim 1, wherein the cDNA is amplified with a first set of primers complementary to sequences contained in regions bridging the deleted sequences in uPAR deletion variants to obtain the amplification product comprising the nucleic acid coding for the at least one uPAR deletion variant, and wherein the cDNA is amplified with a second set of primers complementary to sequences contained in the wild type uPAR to obtain the control amplification product comprising the nucleic acid coding for wild type uPAR.

6. The method according to claim 1, wherein the method provides a prognosis for the tumor associated with the generation of at least one uPAR deletion variant.

7. The method according to claim 6, wherein the prognosis comprises characterization of the tumor, said characterization comprising indicating whether the tumor is more invasive, is more likely to have metastasis, is more likely to have a shorter disease free survival period or is more likely to have a higher rate of recurrence than a tumor not associated with the generation of uPAR deletion variants.

8. A method of providing a prognosis for a breast tumor-bearing patient comprising the steps of:
   (a) obtaining a cDNA containing sample from a breast tumor of said patient,
   (b) analyzing the cDNA of said sample to determine whether alternative splicing of uPAR has occurred and at least one uPAR deletion variant has been generated, wherein the at least one uPAR deletion variant is del4+5, and
   (c) correlating the presence of the at least one uPAR deletion variant in the tumor of the patient with a prognosis of the patient.

9. The method according to claim 8, wherein the step of analyzing the cDNA of said sample comprises: amplifying the cDNA to obtain a quantified control amplification product comprising the nucleic acid coding for wild type uPAR and a quantified amplification product comprising the nucleic acid coding for the at least one uPAR deletion variant, and determining the ratio of wild type uPAR:uPAR deletion variant by comparing the quantified amplification products.

10. The method according to claim 9, wherein the amplification of the cDNA is done by real-time RT-PCR amplification.

11. The method according to claim 8, wherein the cDNA is amplified with a first set of primers complementary to sequences contained in regions bridging the deleted sequences in uPAR deletion variants to obtain the amplification product comprising the nucleic acid coding for the at least one uPAR deletion variant, and wherein the cDNA is amplified with a second set of primers complementary to sequences contained in the wild type uPAR to obtain the control amplification product comprising the nucleic acid coding for wild type uPAR.

* * * * *

SEQUENCE LISTING

<160> NUMBER OF SEQ ID NOS: 25

<210> SEQ ID NO 1
<211> LENGTH: 846
<212> TYPE: DNA
<213> ORGANISM: Homo sapiens

<400> SEQUENCE: 1

-continued

```
atgggtcacc cgccgctgct gccgctgctg ctgctgctcc acacctgcgt cccagcctct    60
tggggcctgc ggtgcatgca gtgtaagacc aacggggatt gccgtgtgga agagtgcgcc   120
ctgggacagg acctctgcag gaccacgatc gtgcgcttgt gggaagaagg agaagagctg   180
gagctggtgg agaaaagctg tacccactca gagaagacca acaggaccct gagctatcgg   240
actggcttga agatcaccag ccttaccgag gttgtgtgtg ggttagactt gtgcaaccag   300
ggcaactctg gcgtccaaa ggatgaccgc acctccgtg ctgtggcta ccttcccggc      360
tgcccgggct ccaatggttt ccacaacaac gacaccttcc acttcctgaa atgctgcaac   420
accaccaaat gcaacgaggg cccaatcctg agcttgaaa tctgccgca gaatggccgc    480
cagtgttaca gctgcaaggg gaacagcacc catggatgct cctctgaaga ctttcctc     540
attgactgcc gaggccccat gaatcaatgt ctggtagcca ccggcactca cgaaccgaaa   600
aaccaaagct atatggtaag aggctgtgca accgcctcaa tgtgccaaca tgcccacctg   660
ggtgacgcct tcagcatgaa ccacattgat gtctcctgct gtactaaaag tggctgtaac   720
cacccagacc tggatgtcca gtaccgcagt ggggctgctc ctcagcctgg ccctgcccat   780
ctcagcctca ccatcaccct gctaatgact gccagactgt ggggaggcac tctcctctgg   840
acctaa                                                              846
```

<210> SEQ ID NO 2
<211> LENGTH: 281
<212> TYPE: PRT
<213> ORGANISM: Homo sapiens

<400> SEQUENCE: 2

```
Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Pro Lys Asp Asp Arg His Leu
            100                 105                 110

Arg Gly Cys Gly Tyr Leu Pro Gly Cys Pro Gly Ser Asn Gly Phe His
        115                 120                 125

Asn Asn Asp Thr Phe His Phe Leu Lys Cys Cys Asn Thr Thr Lys Cys
    130                 135                 140

Asn Glu Gly Pro Ile Leu Glu Leu Glu Asn Leu Pro Gln Asn Gly Arg
145                 150                 155                 160

Gln Cys Tyr Ser Cys Lys Gly Asn Ser Thr His Gly Cys Ser Ser Glu
                165                 170                 175

Glu Thr Phe Leu Ile Asp Cys Arg Gly Pro Met Asn Gln Cys Leu Val
            180                 185                 190

Ala Thr Gly Thr His Glu Pro Lys Asn Gln Ser Tyr Met Val Arg Gly
        195                 200                 205

Cys Ala Thr Ala Ser Met Cys Gln His Ala His Leu Gly Asp Ala Phe
    210                 215                 220
```

Ser Met Asn His Ile Asp Val Ser Cys Cys Thr Lys Ser Gly Cys Asn
225                 230                 235                 240

His Pro Asp Leu Asp Val Gln Tyr Arg Ser Gly Ala Ala Pro Gln Pro
            245                 250                 255

Gly Pro Ala His Leu Ser Leu Thr Ile Thr Leu Met Thr Ala Arg
            260                 265                 270

Leu Trp Gly Gly Thr Leu Leu Trp Thr
        275                 280

<210> SEQ ID NO 3
<211> LENGTH: 711
<212> TYPE: DNA
<213> ORGANISM: Homo sapiens

<400> SEQUENCE: 3
atgggtcacc cgccgctgct gccgctgctg ctgctgctcc acacctgcgt cccagcctct      60
tggggcctgc ggtgcatgca gtgtaagacc aacggggatt gccgtgtgga agagtgcgcc     120
ctgggacagg acctctgcag gaccacgatc gtgcgcttgt gggaagaagg agaagagctg     180
gagctggtgg agaaaagctg tacccactca gagaagacca caggaccct gagctatcgg      240
actggcttga agatcaccag ccttaccgag gttgtgtgtg ggttagactt gtgcaaccag     300
ggcaactctg tcctggagct tgaaaatctg ccgcagaatg gccgccagtg ttacagctgc     360
aaggggaaca gcacccatgg atgctcctct gaagagactt tcctcattga ctgccgaggc     420
cccatgaatc aatgtctggt agccaccggc actcacgaac cgaaaaacca agctatatg      480
gtaagaggct gtgcaaccgc ctcaatgtgc aacatgccc acctgggtga cgccttcagc     540
atgaaccaca ttgatgtctc ctgctgtact aaaagtggg gtaaccaccc agacctggat     600
gtccagtacc gcagtggggc tgctcctcag cctggccctg ccatctcag cctcaccatc      660
accctgctaa tgactgccag actgtgggga ggcactctcc tctggaccta a              711

<210> SEQ ID NO 4
<211> LENGTH: 236
<212> TYPE: PRT
<213> ORGANISM: Homo sapiens

<400> SEQUENCE: 4

Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Val Leu Glu Leu Glu Asn Leu Pro Gln
            100                 105                 110

Asn Gly Arg Gln Cys Tyr Ser Cys Lys Gly Asn Ser Thr His Gly Cys
        115                 120                 125

Ser Ser Glu Glu Thr Phe Leu Ile Asp Cys Arg Gly Pro Met Asn Gln
    130                 135                 140

-continued

```
Cys Leu Val Ala Thr Gly Thr His Glu Pro Lys Asn Gln Ser Tyr Met
145                 150                 155                 160

Val Arg Gly Cys Ala Thr Ala Ser Met Cys Gln His Ala His Leu Gly
                165                 170                 175

Asp Ala Phe Ser Met Asn His Ile Asp Val Ser Cys Cys Thr Lys Ser
            180                 185                 190

Gly Cys Asn His Pro Asp Leu Asp Val Gln Tyr Arg Ser Gly Ala Ala
        195                 200                 205

Pro Gln Pro Gly Pro Ala His Leu Ser Leu Thr Ile Thr Leu Leu Met
    210                 215                 220

Thr Ala Arg Leu Trp Gly Gly Thr Leu Leu Trp Thr
225                 230                 235
```

<210> SEQ ID NO 5
<211> LENGTH: 873
<212> TYPE: DNA
<213> ORGANISM: Homo sapiens

<400> SEQUENCE: 5

```
atgggtcacc cgccgctgct gccgctgctg ctgctgctcc acacctgcgt cccagcctct     60
tggggcctgc ggtgcatgca gtgtaagacc aacggggatt gccgtgtgga agagtgcgcc    120
ctgggacagg acctctgcag gaccacgatc gtgcgcttgt gggaagaagg agaagagctg    180
gagctggtgg agaaaagctg tacccactca gagaagacca acaggaccct gagctatcgg    240
actggcttga agatcaccag ccttaccgag gttgtgtgtg ggttagactt gtgcaaccag    300
ggcaactctg gccgggctgt cacctattcc cgaagccgtt acctcgaatg catttcctgt    360
ggctcatcag acatgagctg tgagaggggc cggcaccaga gcctgcagtg ccgcagccct    420
gaagaacagt gcctggatgt ggtgacccac tggatccagg aaggtgaaga agtcctggag    480
cttgaaaatc tgccgcagaa tggccgccag tgttacagct gcaaggggaa cagcacccat    540
ggatgctcct ctgaagagac tttcctcatt gactgccgag ccccatgaa tcaatgtctg    600
gtagccaccg gcactcacga accgaaaaac caaagctata tggtaagagg ctgtgcaacc    660
gcctcaatgt gccaacatgc ccacctgggt gacgccttca gcatgaacca cattgatgtc    720
tcctgctgta ctaaaagtgg ctgtaaccac ccagacctgg atgtccagta ccgcagtggg    780
gctgctcctc agcctggccc tgcccatctc agcctcacca tcaccctgct aatgactgcc    840
agactgtggg gaggcactct cctctggacc taa                                 873
```

<210> SEQ ID NO 6
<211> LENGTH: 290
<212> TYPE: PRT
<213> ORGANISM: Homo sapiens

<400> SEQUENCE: 6

```
Met Gly His Pro Pro Leu Leu Pro Leu Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80
```

```
Thr Gly Leu Lys Ile Thr Ser Leu Thr Glu Val Val Cys Gly Leu Asp
                85                  90                  95
Leu Cys Asn Gln Gly Asn Ser Gly Arg Ala Val Thr Tyr Ser Arg Ser
            100                 105                 110
Arg Tyr Leu Glu Cys Ile Ser Cys Gly Ser Ser Asp Met Ser Cys Glu
        115                 120                 125
Arg Gly Arg His Gln Ser Leu Gln Cys Arg Ser Pro Glu Glu Gln Cys
    130                 135                 140
Leu Asp Val Val Thr His Trp Ile Gln Glu Gly Glu Glu Val Leu Glu
145                 150                 155                 160
Leu Glu Asn Leu Pro Gln Asn Gly Arg Gln Cys Tyr Ser Cys Lys Gly
                165                 170                 175
Asn Ser Thr His Gly Cys Ser Ser Glu Glu Thr Phe Leu Ile Asp Cys
            180                 185                 190
Arg Gly Pro Met Asn Gln Cys Leu Val Ala Thr Gly Thr His Glu Pro
        195                 200                 205
Lys Asn Gln Ser Tyr Met Val Arg Gly Cys Ala Thr Ala Ser Met Cys
    210                 215                 220
Gln His Ala His Leu Gly Asp Ala Phe Ser Met Asn His Ile Asp Val
225                 230                 235                 240
Ser Cys Cys Thr Lys Ser Gly Cys Asn His Pro Asp Leu Asp Val Gln
                245                 250                 255
Tyr Arg Ser Gly Ala Ala Pro Gln Pro Gly Pro Ala His Leu Ser Leu
            260                 265                 270
Thr Ile Thr Leu Leu Met Thr Ala Arg Leu Trp Gly Gly Thr Leu Leu
        275                 280                 285
Trp Thr
    290

<210> SEQ ID NO 7
<211> LENGTH: 1008
<212> TYPE: DNA
<213> ORGANISM: Homo sapiens

<400> SEQUENCE: 7
atgggtcacc cgccgctgct gccgctgctg ctgctgctcc acacctgcgt cccagcctct      60
tggggcctgc ggtgcatgca gtgtaagacc aacggggatt gccgtgtgga agagtgcgcc     120
ctgggacagg acctctgcag gaccacgatc gtgcgcttgt ggaagaagg agaagagctg     180 gagctggtgg agaaaagctg tacccactca gagaagacca caggaccct gagctatcgg     240 actggcttga agatcaccag ccttaccgag gttgtgtgtg ggttagactt gtgcaaccag     300
ggcaactctg gcgggctgt cacctattcc gaagccgtt acctcgaatg catttcctgt     360
ggctcatcag acatgagctg tgagagggc cggcaccaga gctgcagtg ccgcagccct     420 gaagaacagt gcctggatgt ggtgacccac tggatccagg aaggtgaaga agggcgtcca     480
aaggatgacc gccacctccg tggctgtggc taccttcccg gctgcccggg ctccaatggt     540
ttccacaaca cgacaccctt ccacttcctg aaatgctgca caccaccaa atgcaacgag     600 gcccaatcc tggagcttga aaatctgccg cagaatggcc gccagtgtta cagctgcaag     660
gggaacagca cccatggatg ctcctctgaa gagactttcc tcattgactg ccgaggcccc     720
atgaatcaat gtctggtagc caccggcact cacgaaccga aaaaccaaag ctatatggta     780
agaggctgtg caaccgcctc aatgtgccaa catgcccacc tgggtgacgc cttcagcatg     840
```

-continued

```
aaccacattg atgtctcctg ctgtactaaa agtggctgta accacccaga cctggatgtc      900
cagtaccgca gtggggctgc tcctcagcct ggccctgccc atctcagcct caccatcacc      960
ctgctaatga ctgccagact gtggggaggc actctcctct ggacctaa                  1008
```

<210> SEQ ID NO 8
<211> LENGTH: 335
<212> TYPE: PRT
<213> ORGANISM: Homo sapiens

<400> SEQUENCE: 8

```
Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Val Glu
    50                  55                  60

Lys Ser Cys Thr His Ser Glu Lys Thr Asn Arg Thr Leu Ser Tyr Arg
65              70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145             150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Lys Gly Asn Ser Thr
    210                 215                 220

His Gly Cys Ser Ser Glu Glu Thr Phe Leu Ile Asp Cys Arg Gly Pro
225             230                 235                 240

Met Asn Gln Cys Leu Val Ala Thr Gly Thr His Glu Pro Lys Asn Gln
                245                 250                 255

Ser Tyr Met Val Arg Gly Cys Ala Thr Ala Ser Met Cys Gln His Ala
            260                 265                 270

His Leu Gly Asp Ala Phe Ser Met Asn His Ile Asp Val Ser Cys Cys
        275                 280                 285

Thr Lys Ser Gly Cys Asn His Pro Asp Leu Asp Val Gln Tyr Arg Ser
    290                 295                 300

Gly Ala Ala Pro Gln Pro Gly Pro Ala His Leu Ser Leu Thr Ile Thr
305                 310                 315                 320

Leu Leu Met Thr Ala Arg Leu Trp Gly Gly Thr Leu Leu Trp Thr
                325                 330                 335
```

<210> SEQ ID NO 9

<211> LENGTH: 281
<212> TYPE: PRT
<213> ORGANISM: Homo sapiens

<400> SEQUENCE: 9

```
Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
            85                  90                  95

Leu Cys Asn Gln Gly Asn Ser Gly Arg Pro Lys Asp Asp Arg His Leu
            100                 105                 110

Arg Gly Cys Gly Tyr Leu Pro Gly Cys Pro Gly Ser Asn Gly Phe His
        115                 120                 125

Asn Asn Asp Thr Phe His Phe Leu Lys Cys Cys Asn Thr Thr Lys Cys
130                 135                 140

Asn Glu Gly Pro Ile Leu Glu Leu Glu Asn Leu Pro Gln Asn Gly Arg
145                 150                 155                 160

Gln Cys Tyr Ser Cys Lys Gly Asn Ser Thr His Gly Cys Ser Ser Glu
                165                 170                 175

Glu Thr Phe Leu Ile Asp Cys Arg Gly Pro Met Asn Gln Cys Leu Val
            180                 185                 190

Ala Thr Gly Thr His Glu Pro Lys Asn Gln Ser Tyr Met Val Arg Gly
        195                 200                 205

Cys Ala Thr Ala Ser Met Cys Gln His Ala His Leu Gly Asp Ala Phe
    210                 215                 220

Ser Met Asn His Ile Asp Val Ser Cys Cys Thr Lys Ser Gly Cys Asn
225                 230                 235                 240

His Pro Asp Leu Asp Val Gln Tyr Arg Ser Gly Ala Ala Pro Gln Pro
                245                 250                 255

Gly Pro Ala His Leu Ser Leu Thr Ile Thr Leu Leu Met Thr Ala Arg
            260                 265                 270

Leu Trp Gly Gly Thr Leu Leu Trp Thr
            275                 280
```

<210> SEQ ID NO 10
<211> LENGTH: 235
<212> TYPE: PRT
<213> ORGANISM: Homo sapiens

<400> SEQUENCE: 10

```
Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60
```

```
Lys Ser Cys Thr His Ser Glu Lys Thr Asn Arg Thr Leu Ser Tyr Arg
 65                  70                  75                  80

Thr Gly Leu Lys Ile Thr Ser Leu Thr Glu Val Val Cys Gly Leu Asp
                 85                  90                  95

Leu Cys Asn Gln Gly Asn Ser Leu Glu Leu Glu Asn Leu Pro Gln Asn
            100                 105                 110

Gly Arg Gln Cys Tyr Ser Cys Lys Gly Asn Ser Thr His Gly Cys Ser
        115                 120                 125

Ser Glu Glu Thr Phe Leu Ile Asp Cys Arg Gly Pro Met Asn Gln Cys
130                 135                 140

Leu Val Ala Thr Gly Thr His Glu Pro Lys Asn Gln Ser Tyr Met Val
145                 150                 155                 160

Arg Gly Cys Ala Thr Ala Ser Met Cys Gln His Ala His Leu Gly Asp
                165                 170                 175

Ala Phe Ser Met Asn His Ile Asp Val Ser Cys Cys Thr Lys Ser Gly
            180                 185                 190

Cys Asn His Pro Asp Leu Asp Val Gln Tyr Arg Ser Gly Ala Ala Pro
        195                 200                 205

Gln Pro Gly Pro Ala His Leu Ser Leu Thr Ile Thr Leu Leu Met Thr
    210                 215                 220

Ala Arg Leu Trp Gly Gly Thr Leu Leu Trp Thr
225                 230                 235

<210> SEQ ID NO 11
<211> LENGTH: 289
<212> TYPE: PRT
<213> ORGANISM: Homo sapiens

<400> SEQUENCE: 11

Met Gly His Pro Pro Leu Leu Pro Leu Leu Leu Leu His Thr Cys
  1               5                  10                  15

Val Pro Ala Ser Trp Gly Leu Arg Cys Met Gln Cys Lys Thr Asn Gly
                 20                  25                  30

Asp Cys Arg Val Glu Glu Cys Ala Leu Gly Gln Asp Leu Cys Arg Thr
             35                  40                  45

Thr Ile Val Arg Leu Trp Glu Glu Gly Glu Glu Leu Glu Leu Val Glu
 50                  55                  60

Lys Ser Cys Thr His Ser Glu Lys Thr Asn Arg Thr Leu Ser Tyr Arg
 65                  70                  75                  80

Thr Gly Leu Lys Ile Thr Ser Leu Thr Glu Val Val Cys Gly Leu Asp
                 85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
130                 135                 140

Leu Asp Val Val Thr His Trp Ile Gln Glu Gly Glu Glu Leu Glu Leu
145                 150                 155                 160

Glu Asn Leu Pro Gln Asn Gly Arg Gln Cys Tyr Ser Cys Lys Gly Asn
                165                 170                 175

Ser Thr His Gly Cys Ser Ser Glu Glu Thr Phe Leu Ile Asp Cys Arg
            180                 185                 190

Gly Pro Met Asn Gln Cys Leu Val Ala Thr Gly Thr His Glu Pro Lys
```

-continued

```
                195                 200                 205
Asn Gln Ser Tyr Met Val Arg Gly Cys Ala Thr Ala Ser Met Cys Gln
    210                 215                 220

His Ala His Leu Gly Asp Ala Phe Ser Met Asn His Ile Asp Val Ser
225                 230                 235                 240

Cys Cys Thr Lys Ser Gly Cys Asn His Pro Asp Leu Asp Val Gln Tyr
                245                 250                 255

Arg Ser Gly Ala Ala Pro Gln Pro Gly Pro Ala His Leu Ser Leu Thr
            260                 265                 270

Ile Thr Leu Leu Met Thr Ala Arg Leu Trp Gly Gly Thr Leu Leu Trp
        275                 280                 285

Thr

<210> SEQ ID NO 12
<211> LENGTH: 8
<212> TYPE: PRT
<213> ORGANISM: Homo sapiens

<400> SEQUENCE: 12

Gln Gly Asn Ser Val Leu Glu Leu
1               5

<210> SEQ ID NO 13
<211> LENGTH: 8
<212> TYPE: PRT
<213> ORGANISM: Homo sapiens

<400> SEQUENCE: 13

Gln Gly Asn Ser Gly Arg Pro Lys
1               5

<210> SEQ ID NO 14
<211> LENGTH: 8
<212> TYPE: PRT
<213> ORGANISM: Homo sapiens

<400> SEQUENCE: 14

Glu Gly Glu Glu Val Leu Glu Leu
1               5

<210> SEQ ID NO 15
<211> LENGTH: 16
<212> TYPE: PRT
<213> ORGANISM: Homo sapiens

<400> SEQUENCE: 15

Ala Asp Ser Gln Arg Ile Ala Phe Tyr Arg Leu Leu Asp Glu Phe Phe
1               5                   10                  15

<210> SEQ ID NO 16
<211> LENGTH: 5
<212> TYPE: PRT
<213> ORGANISM: Homo sapiens

<400> SEQUENCE: 16

Ser Arg Ser Arg Tyr
1               5

<210> SEQ ID NO 17
<211> LENGTH: 18
<212> TYPE: DNA
<213> ORGANISM: Homo sapiens
```

```
<400> SEQUENCE: 17
ctccacacct gcgtccca                                                        18

<210> SEQ ID NO 18
<211> LENGTH: 18
<212> TYPE: DNA
<213> ORGANISM: Homo sapiens

<400> SEQUENCE: 18
cttgcagctg taacactg                                                        18

<210> SEQ ID NO 19
<211> LENGTH: 23
<212> TYPE: DNA
<213> ORGANISM: Homo sapiens

<400> SEQUENCE: 19
gacctctgct gcaggaccac gat                                                  23

<210> SEQ ID NO 20
<211> LENGTH: 19
<212> TYPE: DNA
<213> ORGANISM: Homo sapiens

<400> SEQUENCE: 20
aggtaacggc tccgggaat                                                       19

<210> SEQ ID NO 21
<211> LENGTH: 22
<212> TYPE: DNA
<213> ORGANISM: Homo sapiens

<400> SEQUENCE: 21
tttcaagctc caggacagag tt                                                   22

<210> SEQ ID NO 22
<211> LENGTH: 26
<212> TYPE: DNA
<213> ORGANISM: Homo sapiens

<400> SEQUENCE: 22
ggtacagctt ttctccacca gctcca                                               26

<210> SEQ ID NO 23
<211> LENGTH: 24
<212> TYPE: DNA
<213> ORGANISM: Homo sapiens

<400> SEQUENCE: 23
ctcttctcct tcttcccaca agcg                                                 24

<210> SEQ ID NO 24
<211> LENGTH: 21
<212> TYPE: DNA
<213> ORGANISM: Homo sapiens

<400> SEQUENCE: 24
tggtcaccag ggctgctttt a                                                    21

<210> SEQ ID NO 25
<211> LENGTH: 24
<212> TYPE: DNA
```

```
<213> ORGANISM: Homo sapiens

<400> SEQUENCE: 25
tcctggaaga tggtgatggg attt                                              24
```